US012589142B2

(12) United States Patent
Schönharting et al.

(10) Patent No.: US 12,589,142 B2
(45) Date of Patent: Mar. 31, 2026

(54) HLA TUMOR ANTIGEN PEPTIDES OF CLASS I AND II FOR TREATING MAMMARY/BREAST CARCINOMAS

(71) Applicant: PMCR GMBH, Karlsruhe (DE)

(72) Inventors: Wolfgang Schönharting, Bad Wiessee (DE); Sybille Urban, Bad Wiessee (DE)

(73) Assignee: PMCR GMBH, Karlsruhe (DE)

( * ) Notice: Subject to any disclaimer, the term of this patent is extended or adjusted under 35 U.S.C. 154(b) by 1154 days.

(21) Appl. No.: 17/615,595

(22) PCT Filed: Jun. 2, 2020

(86) PCT No.: PCT/EP2020/065235
§ 371 (c)(1),
(2) Date: Dec. 1, 2021

(87) PCT Pub. No.: WO2020/245126
PCT Pub. Date: Dec. 10, 2020

(65) Prior Publication Data
US 2022/0313804 A1     Oct. 6, 2022

(30) Foreign Application Priority Data
Jun. 2, 2019    (DE) ......................... 102019114735.2

(51) Int. Cl.
*A61K 39/00*        (2006.01)
*A61P 15/00*        (2006.01)
*A61P 35/00*        (2006.01)
*C07K 7/02*         (2006.01)

(52) U.S. Cl.
CPC .......... *A61K 39/0011* (2013.01); *A61P 15/00* (2018.01); *A61P 35/00* (2018.01); *C07K 7/02* (2013.01)

(58) Field of Classification Search
CPC ........ G01N 33/57415; A61K 39/39558; A61K 2039/812; C07K 14/70539
See application file for complete search history.

(56) References Cited

FOREIGN PATENT DOCUMENTS

CA          3048108 A1 *  8/2018   ......... A61K 39/0011
WO    WO-2013135266 A1 *  9/2013   ............. A61K 38/10

* cited by examiner

*Primary Examiner* — Gyan Chandra
(74) *Attorney, Agent, or Firm* — Zhigang Ma

(57)     ABSTRACT

The present invention relates to a pharmaceutical composition for use in the treatment or prophylaxis of mammary/breast carcinomas, in particular locally recurring or metastasizing mammary carcinomas in a patient or group of patients, who has or is suspected of having a breast carcinoma, comprising at least 4 to 8 HLA-A tumor antigen peptides corresponding to MHC class I complexes and at least 2 tumor antigen peptides corresponding to MHC class II complexes, wherein the HLA tumor antigen peptides are tumor-exclusive or tumor-associated HLA antigen peptides and are directed against at least one MHC complex including combinations thereof; a pharmaceutical composition, a kit (or parts thereof); a method for determining an HLA peptide of class I and/or II; a method for preparing a pharmaceutical composition according to the invention; and the use of a pharmaceutical composition according to the invention for the preparation of a pharmaceutical composition for the treatment of malignancies, leukemias and neoplasms.

4 Claims, 3 Drawing Sheets
Specification includes a Sequence Listing.

T cell receptor

HLA-A peptide
(7-11 amino-acid
residues)

MHC class I molecules

Protein-binding groove $\alpha_2$          $\alpha_1$

● „Anchor residues"

T cell receptor

HLA-B peptide
(12-17 amino-acid
residues)

MHC class II molecules

Protein-binding groove $\beta$          $\alpha$

■ „Anchor residues"

```
                        SEQUENCE LISTING

<160> NUMBER OF SEQ ID NOS: 48

<210> SEQ ID NO 1
<211> LENGTH: 11
<212> TYPE: PRT
<213> ORGANISM: Artificial Sequence
<220> FEATURE:
<223> OTHER INFORMATION: HLA-A antigen peptide

<400> SEQUENCE: 1

Cys Val Gly Arg Arg Asn Tyr Arg Phe Phe Tyr
1               5                   10

<210> SEQ ID NO 2
<211> LENGTH: 9
<212> TYPE: PRT
<213> ORGANISM: Artificial Sequence
<220> FEATURE:
<223> OTHER INFORMATION: HLA-A antigen peptide

<400> SEQUENCE: 2

His Ala Val Phe Val Gln Ser Tyr Tyr
1               5

<210> SEQ ID NO 3
<211> LENGTH: 8
<212> TYPE: PRT
<213> ORGANISM: Artificial Sequence
<220> FEATURE:
<223> OTHER INFORMATION: HLA-A antigen peptide

<400> SEQUENCE: 3

Leu Leu Asp Pro Glu Asp Val Asp
1               5

<210> SEQ ID NO 4
<211> LENGTH: 8
<212> TYPE: PRT
<213> ORGANISM: Artificial Sequence
<220> FEATURE:
<223> OTHER INFORMATION: HLA-A antigen peptide

<400> SEQUENCE: 4

His Thr Asp Ile Tyr Ala Asn Tyr
1               5

<210> SEQ ID NO 5
<211> LENGTH: 8
<212> TYPE: PRT
<213> ORGANISM: Artificial Sequence
<220> FEATURE:
<223> OTHER INFORMATION: HLA-A antigen peptide
```

-continued

```
<400> SEQUENCE: 5

Ala Val Phe Val Gln Ser Tyr Tyr
1               5

<210> SEQ ID NO 6
<211> LENGTH: 10
<212> TYPE: PRT
<213> ORGANISM: Artificial Sequence
<220> FEATURE:
<223> OTHER INFORMATION: HLA-B antigen peptide

<400> SEQUENCE: 6

Glu Glu Glu Ala Ala Ala Ala Ala Ala Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: HLA-B antigen peptide

<400> SEQUENCE: 7

Met Glu Val Leu Ser Gln Glu Ile Val Arg
1               5                   10

<210> SEQ ID NO 8
<211> LENGTH: 9
<212> TYPE: PRT
<213> ORGANISM: Artificial Sequence
<220> FEATURE:
<223> OTHER INFORMATION: HLA-B antigen peptide

<400> SEQUENCE: 8

His Met Lys Lys Met Met Lys Asp Leu
1               5

<210> SEQ ID NO 9
<211> LENGTH: 10
<212> TYPE: PRT
<213> ORGANISM: Artificial Sequence
<220> FEATURE:
<223> OTHER INFORMATION: HLA-C antigen peptide

<400> SEQUENCE: 9

Ser Ser Thr Ala Leu His Pro Cys Pro Phe
1               5                   10

<210> SEQ ID NO 10
<211> LENGTH: 9
<212> TYPE: PRT
<213> ORGANISM: Artificial Sequence
<220> FEATURE:
<223> OTHER INFORMATION: HLA-C antigen peptide

<400> SEQUENCE: 10

Leu Ser Tyr Leu His Val His Thr Ala
1               5

<210> SEQ ID NO 11
<211> LENGTH: 9
<212> TYPE: PRT
<213> ORGANISM: Artificial Sequence
<220> FEATURE:
<223> OTHER INFORMATION: HLA-C antigen peptide

<400> SEQUENCE: 11
```

Tyr Ser Leu Leu Ser Leu Leu His Thr
1               5

<210> SEQ ID NO 12
<211> LENGTH: 10
<212> TYPE: PRT
<213> ORGANISM: Artificial Sequence
<220> FEATURE:
<223> OTHER INFORMATION: HLA-C antigen peptide

<400> SEQUENCE: 12

Cys Pro Phe Thr His Gly Ser Ser Pro Met
1               5                   10

<210> SEQ ID NO 13
<211> LENGTH: 11
<212> TYPE: PRT
<213> ORGANISM: Artificial Sequence
<220> FEATURE:
<223> OTHER INFORMATION: HLA-A neoantigen peptide

<400> SEQUENCE: 13

Tyr Val Gly Arg Arg Asn Tyr Arg Phe Phe Tyr
1               5                   10

<210> SEQ ID NO 14
<211> LENGTH: 9
<212> TYPE: PRT
<213> ORGANISM: Artificial Sequence
<220> FEATURE:
<223> OTHER INFORMATION: HLA-A neoantigen peptide

<400> SEQUENCE: 14

His Val Val Phe Val Gln Ser Tyr Tyr
1               5

<210> SEQ ID NO 15
<211> LENGTH: 8
<212> TYPE: PRT
<213> ORGANISM: Artificial Sequence
<220> FEATURE:
<223> OTHER INFORMATION: HLA-A neoantigen peptide

<400> SEQUENCE: 15

Leu Leu Asp Pro Glu Asp Val Tyr
1               5

<210> SEQ ID NO 16
<211> LENGTH: 8
<212> TYPE: PRT
<213> ORGANISM: Artificial Sequence
<220> FEATURE:
<223> OTHER INFORMATION: HLA-A neoantigen peptide

<400> SEQUENCE: 16

His Met Asp Ile Tyr Ala Asn Tyr
1               5

<210> SEQ ID NO 17
<211> LENGTH: 8
<212> TYPE: PRT
<213> ORGANISM: Artificial Sequence
<220> FEATURE:
<223> OTHER INFORMATION: HLA-A neoantigen peptide

<400> SEQUENCE: 17

```
Val Val Phe Val Gln Ser Tyr Tyr
1               5

<210> SEQ ID NO 18
<211> LENGTH: 9
<212> TYPE: PRT
<213> ORGANISM: Artificial Sequence
<220> FEATURE:
<223> OTHER INFORMATION: HLA-A neoantigen peptide

<400> SEQUENCE: 18

Asp Glu Asp Glu Ile Lys Trp Trp Trp
1               5

<210> SEQ ID NO 19
<211> LENGTH: 9
<212> TYPE: PRT
<213> ORGANISM: Artificial Sequence
<220> FEATURE:
<223> OTHER INFORMATION: HLA-A neoantigen peptide

<400> SEQUENCE: 19

Phe Val Asn Asp Lys Phe Met Pro Leu
1               5

<210> SEQ ID NO 20
<211> LENGTH: 10
<212> TYPE: PRT
<213> ORGANISM: Artificial Sequence
<220> FEATURE:
<223> OTHER INFORMATION: HLA-B neoantigen peptide

<400> SEQUENCE: 20

Glu Glu Ala Ala Ala Ala Ala Ala Ala Tyr
1               5                   10

<210> SEQ ID NO 21
<211> LENGTH: 10
<212> TYPE: PRT
<213> ORGANISM: Artificial Sequence
<220> FEATURE:
<223> OTHER INFORMATION: HLA-B neoantigen peptide

<400> SEQUENCE: 21

Met Glu Val Leu Ser Gln Glu Ile Val Trp
1               5                   10

<210> SEQ ID NO 22
<211> LENGTH: 9
<212> TYPE: PRT
<213> ORGANISM: Artificial Sequence
<220> FEATURE:
<223> OTHER INFORMATION: HLA-B neoantigen peptide

<400> SEQUENCE: 22

His Met Lys Lys Met Met Lys Ala Leu
1               5

<210> SEQ ID NO 23
<211> LENGTH: 10
<212> TYPE: PRT
<213> ORGANISM: Artificial Sequence
<220> FEATURE:
<223> OTHER INFORMATION: HLA-C neoantigen peptide

<400> SEQUENCE: 23

Ser Ser Thr Pro Leu His Pro Tyr Pro Phe
```

-continued

```
1               5               10
```

```
<210> SEQ ID NO 24
<211> LENGTH: 9
<212> TYPE: PRT
<213> ORGANISM: Artificial Sequence
<220> FEATURE:
<223> OTHER INFORMATION: HLA-C neoantigen peptide

<400> SEQUENCE: 24

Phe Ser Tyr Leu His Val His Thr Ala
1               5

<210> SEQ ID NO 25
<211> LENGTH: 9
<212> TYPE: PRT
<213> ORGANISM: Artificial Sequence
<220> FEATURE:
<223> OTHER INFORMATION: HLA-C neoantigen peptide

<400> SEQUENCE: 25

Tyr Ser Leu Leu Ser Leu Leu His Met
1               5

<210> SEQ ID NO 26
<211> LENGTH: 10
<212> TYPE: PRT
<213> ORGANISM: Artificial Sequence
<220> FEATURE:
<223> OTHER INFORMATION: HLA-C neoantigen peptide

<400> SEQUENCE: 26

Tyr Pro Phe Thr His Gly Ser Ser Pro Met
1               5               10

<210> SEQ ID NO 27
<211> LENGTH: 11
<212> TYPE: PRT
<213> ORGANISM: Artificial Sequence
<220> FEATURE:
<223> OTHER INFORMATION: HLA-A neoantigen peptide

<400> SEQUENCE: 27

Thr Tyr Leu Pro Thr Asn Ala Ser Leu Ser Phe
1               5               10

<210> SEQ ID NO 28
<211> LENGTH: 9
<212> TYPE: PRT
<213> ORGANISM: Artificial Sequence
<220> FEATURE:
<223> OTHER INFORMATION: class I neoantigen peptide

<400> SEQUENCE: 28

Asp Ala Val Ile Val Lys Leu Glu Ile
1               5

<210> SEQ ID NO 29
<211> LENGTH: 9
<212> TYPE: PRT
<213> ORGANISM: Artificial Sequence
<220> FEATURE:
<223> OTHER INFORMATION: class I neoantigen peptide

<400> SEQUENCE: 29

Tyr Tyr Leu Asp Leu Ser Ile Thr Arg
1               5
```

```
<210> SEQ ID NO 30
<211> LENGTH: 10
<212> TYPE: PRT
<213> ORGANISM: Artificial Sequence
<220> FEATURE:
<223> OTHER INFORMATION: class I HLA-A neoantigen peptide

<400> SEQUENCE: 30

Ile Leu Phe Gly Ile Ser Leu Arg Glu Val
1               5                   10

<210> SEQ ID NO 31
<211> LENGTH: 9
<212> TYPE: PRT
<213> ORGANISM: Artificial Sequence
<220> FEATURE:
<223> OTHER INFORMATION: class I HLA-A neoantigen peptide

<400> SEQUENCE: 31

Lys Val Val Glu Phe Leu Ala Met Leu
1               5

<210> SEQ ID NO 32
<211> LENGTH: 9
<212> TYPE: PRT
<213> ORGANISM: Artificial Sequence
<220> FEATURE:
<223> OTHER INFORMATION: class I HLA-A neoantigen peptide

<400> SEQUENCE: 32

Phe Val Asn Asp Lys Phe Met Pro Leu
1               5

<210> SEQ ID NO 33
<211> LENGTH: 9
<212> TYPE: PRT
<213> ORGANISM: Artificial Sequence
<220> FEATURE:
<223> OTHER INFORMATION: class I HLA-A neoantigen peptide

<400> SEQUENCE: 33

Phe Leu Leu Ile Leu Lys Arg Asp Ser
1               5

<210> SEQ ID NO 34
<211> LENGTH: 9
<212> TYPE: PRT
<213> ORGANISM: Artificial Sequence
<220> FEATURE:
<223> OTHER INFORMATION: class I HLA-A neoantigen peptide

<400> SEQUENCE: 34

Arg Thr Pro Leu Ser Ala Leu Cys Val
1               5

<210> SEQ ID NO 35
<211> LENGTH: 9
<212> TYPE: PRT
<213> ORGANISM: Artificial Sequence
<220> FEATURE:
<223> OTHER INFORMATION: class I HLA-B neoantigen peptide

<400> SEQUENCE: 35

Asp Glu Asp Glu Ile Lys Trp Trp Trp
1               5
```

```
<210> SEQ ID NO 36
<211> LENGTH: 17
<212> TYPE: PRT
<213> ORGANISM: Artificial Sequence
<220> FEATURE:
<223> OTHER INFORMATION: class II HLA neoantigen peptide

<400> SEQUENCE: 36

Glu Asp Lys Lys Ile Asp Phe Ser Glu Phe Leu Ser Leu Leu Gly Asp
1               5                   10                  15

Ile

<210> SEQ ID NO 37
<211> LENGTH: 17
<212> TYPE: PRT
<213> ORGANISM: Artificial Sequence
<220> FEATURE:
<223> OTHER INFORMATION: class II HLA neoantigen peptide

<400> SEQUENCE: 37

Ile His Arg Glu Asp Glu Asp Glu Ile Lys Trp Trp Trp Ala Arg Leu
1               5                   10                  15

Asn

<210> SEQ ID NO 38
<211> LENGTH: 17
<212> TYPE: PRT
<213> ORGANISM: Artificial Sequence
<220> FEATURE:
<223> OTHER INFORMATION: class II HLA neoantigen peptide

<400> SEQUENCE: 38

Ser Thr Lys Tyr Ser His Lys Ser Pro Gln Leu Ser Val His Val Thr
1               5                   10                  15

Asp

<210> SEQ ID NO 39
<211> LENGTH: 30
<212> TYPE: PRT
<213> ORGANISM: Artificial Sequence
<220> FEATURE:
<223> OTHER INFORMATION: class II HLA neoantigen peptide

<400> SEQUENCE: 39

Lys Tyr Ile Gln Glu Ser Gln Ala Leu Ala Lys Arg Ser Cys Gly Leu
1               5                   10                  15

Phe Gln Lys Leu Gly Glu Tyr Tyr Leu Gln Asn Ala Phe Leu
            20                  25                  30

<210> SEQ ID NO 40
<211> LENGTH: 14
<212> TYPE: PRT
<213> ORGANISM: Artificial Sequence
<220> FEATURE:
<223> OTHER INFORMATION: class II HLA neoantigen peptide

<400> SEQUENCE: 40

Val Asp Leu Ile Val Glu Tyr Glu Ala Phe Pro Lys Pro Glu
1               5                   10

<210> SEQ ID NO 41
<211> LENGTH: 15
<212> TYPE: PRT
<213> ORGANISM: Artificial Sequence
```

-continued

```
<220> FEATURE:
<223> OTHER INFORMATION: class II HLA neoantigen peptide

<400> SEQUENCE: 41

Ala Thr Tyr Ser Gly Ala Gly Tyr Tyr Leu Asp Leu Ser Ile Thr
1               5                   10                  15

<210> SEQ ID NO 42
<211> LENGTH: 17
<212> TYPE: PRT
<213> ORGANISM: Artificial Sequence
<220> FEATURE:
<223> OTHER INFORMATION: class II HLA neoantigen peptide

<400> SEQUENCE: 42

His Gly Ser Ser Phe Phe Leu Leu Ile Leu Lys Arg Asp Ser Ala Phe
1               5                   10                  15

Ile

<210> SEQ ID NO 43
<211> LENGTH: 17
<212> TYPE: PRT
<213> ORGANISM: Artificial Sequence
<220> FEATURE:
<223> OTHER INFORMATION: class II HLA neoantigen peptide

<400> SEQUENCE: 43

Tyr Ser Met Lys Cys Lys Asn Val Val Pro Leu Asn Asp Leu Leu Leu
1               5                   10                  15

Glu

<210> SEQ ID NO 44
<211> LENGTH: 15
<212> TYPE: PRT
<213> ORGANISM: Artificial Sequence
<220> FEATURE:
<223> OTHER INFORMATION: class II HLA neoantigen peptide

<400> SEQUENCE: 44

Pro Leu Gln Ile Ile Leu Met Pro Gln Val Gln Pro Gly Leu Pro
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: class II HLA neoantigen peptide

<400> SEQUENCE: 45

Leu Leu His Thr Glu Tyr Ser Leu Leu Ser Leu Leu His Met Gln
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: class II HLA neoantigen peptide

<400> SEQUENCE: 46

Asn Tyr Leu Ala Glu Glu Ile Thr Val Asp Val Arg Asp Glu Phe
1               5                   10                  15

<210> SEQ ID NO 47
```

-continued

```
<211> LENGTH: 15
<212> TYPE: PRT
<213> ORGANISM: Artificial Sequence
<220> FEATURE:
<223> OTHER INFORMATION: class II HLA neoantigen peptide

<400> SEQUENCE: 47

Arg Glu Ile Asp Val Leu Glu Arg Glu Leu Asn Val Leu Ile Phe
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: class II HLA neoantigen peptide

<400> SEQUENCE: 48

Pro Ser Asn Tyr Gln Pro His Gln Ala Cys Arg Ile Thr Phe Leu
1               5                   10                  15
```

HLA TUMOR ANTIGEN PEPTIDES OF CLASS I AND II FOR TREATING MAMMARY/BREAST CARCINOMAS

TECHNICAL FIELD

The present invention relates to a pharmaceutical composition for use in the treatment or prophylaxis of mammary/breast carcinoma, in particular locally recurrent or metastatic mammary/breast carcinoma in a patient or group of patients suffering from or suspected of suffering from mammary/breast carcinoma, comprising at least 4 to 8 human leukocyte antigen (HLA)-A tumor antigen peptides corresponding to MHC class I complexes (also referred to herein as "HLA-A restricted tumor antigen peptides") and at least 2 tumor antigen peptides corresponding to MHC class II complexes (also referred to herein as "HLA restricted tumor antigen peptides", "HLAs", "amino acid sequences of the invention", "compounds of the invention" and "polypeptides of the invention", respectively, wherein the HLA tumor antigen peptides are tumor-exclusive or tumor-associated HLA antigen peptides and are directed against the corresponding MHC complexes, including combinations thereof (i.e. binding to those or having affinity therefor), a combination preparation (or parts thereof), a method for determining/identifying at least one HLA antigen peptide corresponding to the MHC class I complexes and/or MHC class II complexes for use in the pharmaceutical composition, a method for preparing a pharmaceutical composition according to the invention, and a method for determining the regression, course or occurrence of a mammary/breast cancer disease.

PRIOR ART

Despite interdisciplinary approaches and exhaustion of classical therapies, cancers remain among the leading causes of death. In general, cancer is treated by established methods such as surgical tumor removal (resection), chemotherapy and/or radiotherapy.

In particular, the development of resistance by cancer cells during chemotherapy and/or radiotherapy mostly prevents the complete removal of all cancer cells from a subject's body.

Newer therapeutic concepts aim to include the patient's own immune system in the overall therapeutic concept by using specific measures such as antibody therapy against immunosuppressors and recombinant immunoinformatics (i.e. treatment with information carriers). A prerequisite for the success of such a strategy is the recognition of tumor-specific or tumor-associated antigens or epitopes by the immune system of the subject, whose effector functions (by the immune cells) are to be enhanced. Tumor cells differ biologically significantly from their non-malignant cells of origin. These differences are due to genetic alterations that are acquired during tumor development and, among other things, also lead to the formation of qualitatively or quantitatively altered molecular structures in the tumor cells. If such tumor-associated structures are recognized by the specific immune system of the tumor-bearing host, they are referred to as tumor-associated epitopes.

Cancer/testis antigens (CTAs) refer to a group of tumor-associated proteins expressed by tumors of various histological origins, among others (Fratta et al., Molecular Oncology, 5(2), April 2011, 164-182). In healthy adult vertebrates, expression of these proteins is restricted to male germ cells. However, in cancer, the expression of these developmental antigens is often reactivated and thus can serve as a site of immune activation. Many of the CTAs are oncogenes and are involved in cellular processes such as cell growth and division, inhibition of apoptosis, and metastasis. They are often causative for oncogenesis and malignant transformation and are therefore classified as tumor antigens. The expression of CTAs in different malignancies is heterogeneous and often correlates with tumor progression, which is why they also serve as biomarkers for tumor disease progression. HLA antigen peptides of such CTAs are often presented as degradation products on the surface of tumor cells. It is known that such presentation of CTA-derived HLA antigen peptides can be used for the development of new treatment modalities combining drug treatment with anti-CTA-targeted immunotherapy.

Human leukocyte antigens (also called HLA system, HL antigens, histocompatibility antigens, human leukocyte antigen) are a group of human genes that are central to the function of the immune system. The HLA system is known as the major histocompatibility complex (MHC) and is found in all vertebrates.

There are two types of MHCs, namely class I MHC molecules (herein also referred to as "class I MHC complexes" or "class I HLA complexes") and class II MHC molecules (herein also referred to as "class II MHC complexes" or "class II HLA complexes"). Both are found on the cell surface of all nucleated cells in the bodies of mandibular vertebrates. MHC molecules consist of two polypeptide chains, a heavy $\alpha$-chain and a light $\beta$-chain (see also FIGS. 1 and 2).

Class I MHC molecules are expressed on the cell surface of all nucleated cells and are recognized by CD8+ T cells (also referred to as T killer cells or cytotoxic T cells). Class II MHC molecules are mainly exposed on the cell surface of antigen-presenting cells and are recognized by CD4+ T cells (also referred to as T helper cells).

In blood cells, class I MHC molecules are exposed on the cell surface of platelets (also thrombocytes), but not on red blood cells. Their function is to present peptide fragments of non-self proteins on their cell surface and transfer them out of the cell into killer T cells (also cytotoxic T cells) to trigger an immediate immune system response against a specific non-self antigen presented by means of an MHC class I protein. Because class I MHC molecules present peptides derived from cytosolic proteins, the pathway of presentation of class I MHC molecules is often referred to as the cytosolic or endogenous pathway.

Here, HLA antigen peptides serve as mediators between the corresponding MHC complex presented on the cell surface and the T cell receptor.

Class I HLA complexes (HLA-A, B, and C) present intracellular antigen peptide fragments (herein "HLA antigen peptides corresponding to MHC class I complexes" or "type 1 HLA antigen peptides" comprising 7 to 11, predominantly 9 amino acids—so-called nonamers—in their sequence) towards T killer cells (also cytotoxic T cells), whereas HLA class II complexes (HLA-DR, DQ and DP) present exogenously derived antigen peptides (herein "HLA antigen peptides corresponding to MHC class II complexes" or "HLA antigen peptides of type 2", comprising more than 11 amino acids, preferably 12 to 17 amino acids in their sequence) towards T helper cells. In humans, HLA antigen peptides of class I, corresponding to MHC class I, are subdivided into HLA-A, HLA-B, and HLA-C antigen peptides.

It is known from the prior art that binding of HLA antigen peptides corresponding to MHC class II complexes to the peptide binding pocket of the corresponding class II HLA complexes occurs primarily via the discrete anchor residues in amino acid positions 1, 4, 6/7, and 9 of the HLA antigen peptides (see, e.g., Sinigaglia and Hammer (1995), J. Exp. Med., 181, 449-451). Particularly preferred according to the prior art is the interaction between the peptide binding pocket motif of the class II HLA complex and the discrete anchor residues in amino acid positions 6 and 9 of the HLA antigen peptides corresponding to MHC class II complexes. The amino acid residues in amino acid positions 2, 3, 5, 7, and 8 of the respective HLA antigen peptides are available for interaction with the T-cell receptor (Sant' Angelo et al. (2002), Recognition of core and flanking amino acids of MHC class II-bound peptides by the T-cell receptor, Eur J Immunol, 32(9), 2510-20).

In contrast, for HLA antigen peptides corresponding to MHC class I complexes, the amino acid positions 1, 2, and 9 have been postulated as the primary anchor residues relative to the corresponding class I HLA complex (see, for example, Binkowski et al. (2012), PLoS ONE, 7(8), e41710; Yamada (1999), Tissue Antigens, 54(4), 325-32).

A new study in the USA is currently investigating the specific efficacy of only one HLA antigen peptide in the treatment of cancer (see WO 2013/135266, Inderberg-Suso et al. (2012), Oncoimmunology., 1(5), 670-686 and Slingluff (2011), Cancer J., 17(5), 343-350). Therefore, the therapeutic spectrum is very limited and by applying only one HLA antigen peptide, the efficacy is questionable.

This is particularly true in a tumor entity such as mammary/breast carcinoma, which is characterized by low homogeneity (i.e., high heterogeneity) and lack of initial immunogenicity compared to other tumor entities. Clinically effective targeted immunoinformation and stimulation therapies therefore rely on a multifactorial information approach.

A major disadvantage of cancer immunotherapies is therefore that they are based on the fact that the individual mutation pattern (signatures) of the tumor of each cancer patient must be decoded. Synthetic vaccines, for example RNA-based vaccines, are then produced to match the determined profile of the mutation pattern for each individual patient (so-called vaccine production). The vaccines obtained in this way can then only be used for the individual treatment of this particular patient.

In principle, these novel vaccines in cancer immunotherapy are therefore not suitable for other patients with the same tumor, but can only be used for a single patient whose mutanome was previously analyzed for vaccine production.

Thus, it is a task of the present invention—in contrast to fully individualized cancer immunotherapy—to provide a pharmaceutical composition for different subjects or a specifically predetermined group of patients (i.e., for a specific group of patients with at least one identical HLA allele) who have overlaps in the mutanome of the malignant or neoplastic tissue (mammary/breast carcinoma) (derivation of patient groups).

It is therefore an object of the present invention to provide pharmacologically active agents, as well as pharmaceutical compositions comprising such active agents, which can be used for the diagnosis, prevention and/or treatment of mammary/breast cancer and other diseases and disorders listed herein; and to provide methods for the diagnosis, prevention and/or treatment of such cancers involving the administration and/or use of such agents and compositions.

In particular, it is an object of the invention to provide such pharmacologically active agents, pharmaceutical compositions and/or methods that have certain advantages over the active agents, compositions and/or methods currently in use and/or known in the prior art. These advantages result from the following further description.

In particular, it is an object of the invention to provide therapeutically active HLA antigen peptides which can be used as pharmacologically active HLA antigen peptides or as as pharmacologically active agents, and to provide pharmaceutical compositions containing same, for the diagnosis, prevention and/or treatment of mammary/breast carcinomas and other diseases and disorders, in particular cancers, as set forth herein; and to provide methods for the diagnosis, prevention and/or treatment of such diseases and disorders involving the administration and/or use of such therapeutically active HLA antigen peptides and compositions.

In particular, it is a specific task of the present invention to provide such HLA antigen peptides suitable for prophylactic, therapeutic and/or diagnostic use in warm-blooded animals, especially in a mammal and most particularly in a human.

According to the invention, these tasks are fulfilled by a pharmaceutical composition for use in the treatment or prophylaxis of mammary/breast carcinomas, in particular locally recurrent or metastatic mammary/breast carcinomas in a patient or group of patients suffering from or suspected of suffering from mammary/breast carcinomas, comprising a pharmacologically effective amount of from 4 to 8, preferably 4, 5, 6, 7 or 8 HLA-A tumor antigen peptides corresponding to MHC class I complexes and at least 2, preferably 1, 2, 3 or 4 tumor antigen peptides corresponding to MHC class II complexes, characterized in that the HLA tumor antigen peptides are tumor-exclusive or tumor-associated HLA antigen peptides, solved according to claim 1, wherein the HLA tumor antigen peptides comprise, in particular, sequences contained in the sequences SEQ ID NO. 13-SEQ ID No. 26, SEQ ID No. 28, SEQ ID No. 29 and SEQ ID No. 32-SEQ ID No. 48.

Further advantageous embodiments are given in the subclaims.

According to a particularly preferred embodiment of the present invention, the pharmaceutical composition consists exclusively of a carrier liquid (preferably water, a pharmaceutically acceptable saline solution and/or pharmaceutically DMSO—such compositions of carrier liquids are known to the skilled person and are, for example, in the range around 30% DMSO and 70% water), in which a pharmacologically effective amount of 4 to 8 HLA-A tumor antigen peptides corresponding to the MHC class I complexes and 2 tumor antigen peptides corresponding to the MHC class II complexes are dissolved or suspended, and an adjuvant.

Pharmaceutical composition and suitable dosage forms for application of the pharmaceutically active HLA tumor antigen peptides are prepared according to standard procedures known in the prior art and are readily applicable to any new or improved process for their preparation.

Particularly advantageously, administering the aforementioned combination of a pharmacologically effective amount of the HLA tumor antigen peptides to the patient or group of patients suffering from mammary/breast carcinoma effectively reduces the CA 15-3 level. CA 15-3 (Cancer antigen 15-3) is a so-called glycoprotein used as a specific tumor marker in breast carcinomas. The CA 15-3 value is a laboratory value that rises significantly above the threshold value in certain cancers, especially mammary/breast carcinomas. In healthy individuals, the CA 15-3 threshold is below 31 enzyme units per milliliter (<31 U/ml). Preferably, administering the pharmacologically effective amount of tumor antigen peptides to the patient or group of patients suffering from mammary/breast carcinoma reduces the CA 15-3 value below 60 U/ml, more preferably below 50 U/ml, most preferably to a range below 40 U/ml and a normal value (<31 U/ml).

Particularly preferably, administering the pharmacologically effective amount of HLA tumor antigen peptides to the patient or group of patients thus effectively prolongs the progression-free survival of the individual, preferably by at least 2 to 5 years.

Contrary to conventional approaches, a surprising finding of the present invention is that tumor antigen peptides that have a $K_D$ value in the range of 50 to 500 nM trigger effector cells (i.e., cytotoxic T cells), contrary to conventional in silico binding prediction models that have considered them to have low binding. Rather, it is of particular advantage for the efficacy of the tumor antigen peptides that the HLA tumor antigen peptides used for treatment in the patient or group of patients with at least one identical HLA allele are immunogenic, which can be determined in advance with an immunogenicity test (e.g., by means of Western blot, ELISA techniques, especially by means of ELISPOT, preferably via interferon-gamma, interferon-alpha or interleukin (IL-2), or immunodetection with microscopic analysis).

As described herein, but without limitation to any explanation, mechanism of action, or hypothesis in the present invention, two distinct classes of amino acid sequences of the invention have been determined based on their ability to enhance the interaction of class I MHC complexes and class II MHC complexes, respectively, with at least one T cell receptor (particularly in the detection method described below in embodiment 3). These two classes of amino acid sequences of the invention are (as described below):

"HLA tumor antigen peptides corresponding to MHC class I complexes": (see particularly preferred examples in Tables 1-3).

"HLA tumor antigen peptides corresponding to MHC class II complexes": (see particularly preferred examples in Table 4).

Advantageously, the use/application of the pharmaceutical composition according to the invention or the specific combination of tumor antigen peptides contained therein corresponding to the MHC class I complexes and MHC class II complexes to the patient or group of patients with at least one identical HLA allele is not merely a passive immunization (as in the case of treatment with antibodies, e.g. Herceptin) but an active immunization (i.e. specific activation of the T cells or B helper cells via information carriers). Since the specific activation of class II MHC molecules, which are mainly exposed on the cell surface of antigen-presenting cells, by means of tumor antigen peptides corresponding to MHC class II complexes, CD4+ T cells (also known as T helper cells) and B cells are specifically activated.

For binding to a T cell receptor, an HLA tumor antigen peptide of the invention typically has in its amino acid sequence one or more amino acid residues or one or more segments of amino acid residues (i.e., with each "segment" comprising two or more amino acid residues located adjacent to or in close proximity to each other, i.e. in the primary or tertiary structure of the amino acid sequence) through which the amino acid sequence of the invention can bind to a T cell receptor (in particular a binding pocket thereof), the amino acid residues or portions of the amino acid residues thus forming the "anchor" for binding to a T cell receptor (also referred to herein as "anchor amino acids").

The determination of this "anchor" can be assessed, for example, by in silico methods (e.g., the artificial neural network NNAlign used in the publicly available NetMHC-4.0) or by targeted mutation (insertions or substitutions in the amino acid sequence of HLA tumor antigen peptides).

The HLA tumor antigen peptides provided by the present invention are preferably in substantially isolated form (as defined herein) or form part of a protein or polypeptide, which may comprise or consist essentially of one or more HLA tumor antigen peptides of the invention, and which may optionally further comprise one or more pharmaceutically active HLA tumor antigen peptide(s) (all optionally joined via one or more linkers in a so-called oligopeptide). For example, and without limitation, the tumor antigen peptides of the invention may be used as a binding moiety in such a protein or polypeptide, which may optionally include one or more additional amino acid sequences that may serve as a binding moiety (i.e., against one or more targets other than a T cell receptor) to provide a monovalent, multivalent, or multispecific polypeptide of the invention as described herein, respectively. Such protein or polypeptide may also be in substantially isolated form (as defined herein).

A pharmaceutical composition comprising a specific combination of HLA tumor antigen peptides corresponding to MHC class I complexes and HLA tumor antigen peptides corresponding to MHC class II complexes disclosed herein has been shown to be particularly advantageous as it is capable of specifically activating T cells as well as specifically activating B cells.

In other embodiments, the present invention also relates to a pharmaceutical composition, a kit (or parts thereof), a method for determining/identifying a pharmacologically active HLA antigen peptide corresponding to class I and/or class II MHC complexes, a method for preparing a formulation according to the invention, and the use of a formulation according to the invention for the preparation of a pharmaceutical composition for the treatment of cancer, in particular mammary/breast carcinoma.

In particular, the polypeptides and pharmaceutical compositions of the present invention may be used for the prevention and treatment of cancers, particularly mammary/breast cancers, characterized by mutation(s) (herein "amino acid substitutions") altered wild-type HLA antigen peptides corresponding to MHC class I complexes and/or corresponding to MHC class II complexes (so-called HLA tumor antigen peptides, as defined herein).

In general, prior to the invention, the treatment of cancer of a patient or group of patients is(are) carried out by classical methods such as chemotherapy, radiotherapy and/or cancer immunotherapy.

Classical methods for the treatment of cancers of the invention are, for example, surgical tumor removal (resection), chemotherapy and/or radiation therapy, with two or even all three treatment methods frequently being applied simultaneously to a subject. In cancer immunotherapy methods, a distinction is made between active and passive immunization. In active immunization, the subject is administered substances that are intended to trigger an immune response in his or her immune system. In passive immunization, antibodies or antibody fragments are used. In adoptive immunotherapy (i.e. passive immunotherapy, as comparable to antibody treatment without direct immunomodulation), leukocytes are removed from the subject, cultured ex vivo, and then re-injected into the subject. If the treatment does not destroy all cells of the tumor and its metastases, further treatment of cancer is significantly hampered by the development of resistance.

Thus, the present invention also comprises a pharmaceutical composition for the treatment of cancers, as described above, following the classical methods for the treatment of cancers, namely after unsuccessful surgical tumor removal (resection), chemotherapy and/or radiotherapy.

It is a particular achievement of the inventors to have found that for effective treatment, the HLA-A antigen peptides used in accordance with the invention are actually presented on the cell surface of cells of the malignant tissue to be treated (in particular mammary/breast carcinoma) in the individual to be treated. Therefore, the pharmaceutical composition to be applied comprises HLA antigen peptides presented on the surface of the tumor cells of the patient's or group of patients' mammary/breast carcinoma, which is determined by ultra-high performance liquid chromatography (UHPCL) in combination with ESI mass spectrometry (MS) prior to application and assembly of the pharmaceutical composition. By such ligandom assay, unlike conventional cancer immunotherapies, the binding ability of the HLA-A antigen peptides of the invention towards the corresponding class I or class II MHC complex has already been demonstrated in advance.

According to a preferred embodiment of the invention, at least 60%, preferably at least 80%, most preferably 90%, ideally all of the HLA tumor antigen peptides contained in the pharmaceutical composition to be applied are presented on the surface of the tumor cells of the patient's or group of patients' mammary/breast carcinoma as determined by methods as described herein.

According to a particularly preferred embodiment of the present invention, the HLA antigen peptides corresponding to the MHC class I complexes are selected from the group consisting of the amino acid sequences given in SEQ ID Nos. 1 to 35 or have an amino acid identity of at least 85% with respect to these amino acid sequences.

According to a particularly preferred embodiment of the present invention, the HLA antigen peptide corresponding to MHC class II complexes are selected from the group consisting of the amino acid sequences set forth in SEQ ID Nos. 36 to 48.

It has been found by the inventors of the present invention that the HLA-A antigen peptides explicitly disclosed herein corresponding to MHC class I are particularly suitable for use in the treatment of mammary/breast carcinomas in subjects or a group of patients having at least one identical HLA allele exhibiting subtype A*01 and/or A*02. That is, the HLA-A tumor antigen peptides used herein preferably bind to the corresponding MHC class I complex of subtype A*01 and/or A*02.

According to a particularly preferred embodiment, the individuals (subjects or a group of patients) have the haplotype with the subgroup A*01:01 and/or A*02:01.

Alternatively, the individuals (subjects or a patient group) particularly preferably have the haplotype with the subgroup B*44:01 and/or A*18:01.

It is true that the pharmaceutical composition according to the invention could be used for the tissue-independent treatment of malignancies, neoplasms, and/or leukemias (i.e., unlike conventional preparations, the cancer subtypes do not initially play a role), so that the pharmaceutical composition can be applied across tissues for use as an anticancer drug. However, it was found that the administration/application of the specific combination of 4 to 8 HLA-A tumor antigen peptides and at least 2 HLA tumor antigen peptides corresponding to MHC class I complexes according to the invention can be used particularly advantageously for the treatment of breast cancer.

A further clinical gain in the use of the pharmaceutical composition in the treatment of a patient or of a patient or group of patients having at least one identical HLA allele can be achieved by adding to the pharmaceutical composition, further, a pharmacologically effective amount of at least one HLA-B tumor antigen peptide, preferably 1, 2, 3, 4 or 5 HLA-B tumor antigen peptide(s) corresponding to MHC class I complexes and/or at least one HLA-C tumor antigen peptide, preferably 1, 2, 3, 4 or 5 HLA-C tumor antigen peptide(s) corresponding to MHC class I complexes is added. It is understood that also the HLA-B tumor antigen peptide(s) or HLA-C tumor antigen peptide(s) corresponding to the specific haplotype of the patient or group of patients having at least one identical HLA allele are selected for treatment or prophylaxis.

According to a preferred embodiment of the present invention, the pharmaceutical composition according to the invention comprises at least 6, 7, 8, 9, 10, 11 or 12 HLA antigen peptides corresponding to MHC class I complexes and/or MHC class II complexes and/or at least one HLA antigen peptide which is analogous to at least one HLA antigen peptide exposed on the cell surface of cells from malignant and/or neoplastic tissue (in particular mammary/breast carcinoma) of the individual to be treated, which in its amino acid sequence has at least one amino acid exchange with respect to the wild type of this HLA antigen peptide (so-called neoantigen peptide) and at least a 3-fold increased specific affinity towards the T cell receptor of the endogenous T cells (correspondingly measured and/or expressed as $K_D$ value). Particularly good success was achieved with pharmaceutical compositions that had at least 10, 11 or 12 HLA antigen peptides corresponding to MHC class I complexes and/or MHC class II complexes.

In this regard, it has been shown that pharmaceutical compositions consisting of a pharmacologically effective amount of 4 to 8, preferably 4, 5, 6, 7 or 8 HLA-A and/or HLA-B tumor antigen peptides corresponding to MHC class I complexes, in particular neoantigen peptides thereof, and 1, 2, 3 or 4 tumor antigen peptides corresponding to MHC class II complexes, in particular neoantigen peptides thereof, are particularly preferred.

According to a particularly preferred embodiment of the present invention, at least one HLA-A antigen peptide of the composition is a tumor-exclusive HLA-A antigen peptide (i.e., a cancer-testis antigen (CTA) that does not (no longer) appear beyond the immunoprivileged spermatocytes in the healthy/normal tissue of the patient/group of patients or a so-called neoantigen peptide), and wherein specific binding of the tumor-exclusive HLA-A antigen peptide occurs with a specific dissociation ($K_D$) in the range of 10 to 50 nM, as determined by surface plasmon resonance.

It is also an outstanding achievement of the inventors to have discovered that a pharmaceutical composition based on HLA antigen peptides is particularly effective when both T lymphocytes (T cells for short) and B lymphocytes (B cells for short) are activated by them.

T cells belong to the lymphocyte cell group and play an important role in the human immune system. T cells recognize antigens via a specific receptor, the so-called T cell receptor (TCR). However, for this to happen, the antigen must be offered by an antigen-presenting cell (APC).

Stable binding of the T cell to the antigen-presenting cell requires the participation of so-called auxilliary proteins. These include CD4 and CD8 (CD="Cluster of Differentiation").

T cells carrying the CD4 trait are also called CD4-positive T cells or T helper cells. In normal adult blood, CD4+ T cells account for 27-57% of lymphocytes, or approximately 310-1570 cells/µl.

The group of CD8-positive (CD8+) T cells, which also includes regulatory T cells, contains the cytotoxic T cells or T killer cells. They play a special role in killing the body's own cells that are infected by viruses.

This feature of the cellular immune defense is of crucial importance in the present invention, since the molecular biological and genetic alterations of tumor cells can be recognized and lysed by this T cell population.

In contrast, B cells are the only cells capable of producing antibodies and, together with T cells, make up the crucial component of the adaptive immune system. While T cells are involved in the cell-mediated immune response, B cells are the carriers of the humoral immune response (and are responsible for the formation of antibodies).

A pharmaceutical composition has been shown to comprise the tumor-associated HLA antigen peptides whose expression level in the tumor cells is at least three times higher than in the healthy cells of the patient or the specifically determined group of patients having at least one identical HLA allele, as determined for example by qPCR, and wherein the tumor-associated HLA antigen peptides are associated with proliferation, invasiveness, angiogenesis and an increase in cytokeratin production of the mammary/breast carcinoma, have particularly effective pharmacological effects in the treatment of mammary/breast carcinomas.

Particularly preferably, each individual HLA antigen peptide used herein for the treatment of breast carcinoma is included in the pharmaceutical composition at an absolute concentration (i.e., administration dose) of at least from 100 to 600 µg, preferably from 300 to 600 µg.

In the meantime, it has been shown in further experiments that pharmaceutical compositions containing an absolute concentration of >600 µg per HLA tumor antigen peptide, i.e. at least 700 to 1,200 µg, preferably from 800 to 1,200 µg, are particularly preferred, as this greatly intensifies the information (the activation and/or training of the immune system). This is particularly advantageous if the immune system of the subject to be treated has already been weakened by pretreatment with a standard therapy procedure (e.g. at least one operation, radiation, chemotherapy and/or hormone therapy). In addition, the absolute concentration per HLA tumor antigen peptide is preferred, as this substantially minimizes the influence of degradation of the HLA tumor antigen peptides (e.g., by ligases) after their application to the subject.

It is highly convenient that the pharmaceutical composition comprises an adjuvant which, when the composition is applied to a patient, is capable of forming a granuloma at the site of application. The advantage in the formation of a granuloma is that a depot effect can thus be achieved, whereby the HLA tumor antigen peptides are advantageously stored at the site of application in the manner of a reservoir and can be delivered to the organism of the subject over a longer period of time. Particularly advantageously, therefore, weekly applications of the pharmaceutical composition according to the invention are omitted. Preferably, the application of the pharmaceutical composition for the treatment of cancer diseases within the meaning of the invention, when used over a longer period of time, therefore only has to be carried out every 2 weeks, particularly preferably only once a month.

In this regard, the pharmaceutical composition is preferably applied subcutaneously or intradermally and, preferably substantially simultaneously at at least 2, more preferably at least 3 application sites, typically at 3 to 4 application sites remote from a tumor lesion and/or the cancerous lymph node area.

The essentially simultaneous (successive) application at several application sites has the advantage that, particularly in the case of application of high absolute concentrations of the individual HLA antigen peptides (i.e. administration dose) in the range of >600 µg, which require larger application volumes (>1 mL) for complete dissolution of the individual HLA antigen peptides, the application of the application solution, which has only a limited shelf life after opening, is carried out as simultaneously as possible.

Preferably, the pharmaceutical composition comprising each individual HLA antigen peptide in the composition at an absolute concentration (i.e., administration dose) of 300 to 600 µg need only be administered intradermally or subcutaneously once every 2 weeks, preferably once every 4 weeks, for a period of at least one year to a patient or a specifically identified group of patients having at least one identical HLA allele.

It has been found that a pharmaceutical composition in which at least one HLA tumor antigen peptide has at least one mutation relative to the wild-type HLA tumor antigen peptide (as detailed below) that results in an increase, preferably to <500 nm, most preferably <50 nm of the specific binding affinity to the T cell receptor (KD value) of the individual treated with HLA tumor antigen peptide compared to the wild type of HLA antigen peptide, shows particularly beneficial effects in the treatment of mammary/breast carcinomas.

According to a preferred embodiment of the present invention, the pharmaceutical composition is used for the treatment of breast cancer as monotherapy or in combination with other known therapies and/or compounds for the treatment of breast cancer. In this regard, the pharmaceutical composition will be administered as a first-line therapy to the patient or group of patients with at least one identical HLA allele (so-called adjuvant monotherapy).

Alternatively, it may be provided that the patient or group of patients to be treated with the pharmaceutical composition with at least one identical HLA allele has already received at least one standard therapy procedure (e.g., at least one surgery, radiation, chemotherapy, and/or hormone therapy) in advance.

Particularly preferably, the mammary/breast cancer to be treated is a hormone positive, HER2/neu or triple negative breast cancer.

HLA Tumor Antigen Peptide

Also encompassed by the present invention are HLA tumor antigen peptides corresponding to MHC class I complexes or MHC class II complexes, particularly for use in the treatment or prophylaxis of mammary/breast carcinoma in a patient or group of patients suffering from or suspected of suffering from mammary/breast carcinoma, respectively for a pharmaceutical composition according to the invention, wherein the HLA tumor antigen peptides comprise the amino acid sequences selected from the group consisting of those given in SEQ ID Nos. 13 to 35 and SEQ ID Nos. 36 to 48, in particular those given in SEQ ID No. 13 to SEQ ID No. 26, SEQ ID No. 28, SEQ ID No. 29 and SEQ ID No. 32 to SEQ ID No. 48, or which have at least one mutation, preferably an amino acid substitution, relative to one of these amino acid sequences.

Particularly preferred in this regard is the use of the foregoing HLA tumor antigen peptides in a method of treating breast carcinomas, particularly locally recurrent or metastatic breast carcinomas in a patient or group of patients having at least one identical HLA allele, the method comprising administering/applying to the patient or group of patients a treatment regimen comprising a pharmacologically effective amount of at least one of the foregoing HLA tumor antigen peptides.

In order for the immune system of the individual to whom the HLA tumor antigen peptides or pharmaceutical composition according to the invention is administered to still be fully functional and thus easier to train, it is advantageous if the individual has not yet received radiation, chemotherapy and/or hormone therapy against the breast cancer, especially for locally recurrent or metastatic breast cancer, and/or has not received prior adjuvant chemotherapy in recurrence for 12 months or less since the last dose of a chemotherapeutic agent.

Particularly preferably, the treatment regimen described herein, in particular using at least one aforementioned HLA tumor antigen peptide according to the invention, effectively prolongs the progression-free survival of the individual.

A) HLA-A Antigen Peptides and HLA-A Neoantigen Peptides

An "HLA-A tumor antigen peptide corresponding to MHC class I complexes" is defined herein as an "HLA antigen peptide of the invention" or "amino acid sequence of the invention" (as defined herein) comprising:
 a) an amino acid sequence consisting of 7 to 11 amino acids; and/or
 b) a neoantigen peptide having an amino acid sequence consisting of 7 to 11 amino acids, which is
  i) is analogous to at least one HLA-A antigen peptide exposed on the cell surface of cells from malignant and/or neoplastic tissue (in particular mammary/breast carcinoma) of the individual to be treated, and
  ii) in its amino acid sequence at least one amino acid exchange compared to the wild type of this HLA-A neoantigen peptide (so-called "HLA-A neoantigen peptide") and
  iii) has at least a 3-fold increased specific affinity towards the T cell receptor of endogenous T cells It is an outstanding achievement of the inventors to have recognized that HLA-A neoantigen peptides which in their amino acid sequence compared to the wild type of this HLA-A antigen peptide have at least one amino acid exchange in the amino acid positions 1 (N-terminus), 2, 7/8 and/or the C-terminus, have an at least 4-fold, particularly preferably at least 5-fold, most preferably at least 8-fold increased specific affinity ($K_D$) for the T cell receptor of the endogenous T cells and are therefore particularly preferred for use in the composition according to the invention.

Particularly preferably, the amino acid exchange in the amino acid sequence of the HLA-A antigen peptide is a single amino acid exchange in amino acid position 1 (N-terminus), 2, 7/8, or the C-terminus.

Preferably, the amino acid exchange in the amino acid sequence of the HLA-A neoantigen relative to the wild-type of this HLA-A antigen peptide is a C/Y, NV, D/Y, E/K, P/L, N/D, or T/M exchange.

Preferably, the HLA-A peptide or the HLA-A neoantigen has a specific activity (KD) towards the T cell receptor, as determined by any suitable detection method known to the skilled person in the prior art, of less than 100 nM, more preferably less than 75 nM or most preferably less than 50 nM, such as less than 40 nM, 35 nM, 30 nM, 25 nM or 20 nM.

Preferably, the HLA-A tumor antigen peptide or the HLA-A neoantigen is present in the pharmaceutical composition according to the invention at a concentration, as defined above, of at least 100 to 600 µg, alternatively preferably at an absolute concentration of >600 µg relative to the volume of the pharmaceutical composition to be applied.

Preferably, the HLA-A tumor antigen peptides or HLA-A neoantigens are selected as defined in (b) above.

According to a particularly preferred embodiment, an "HLA-A neoantigen peptide", is preferred, comprising the following scaffold sequence:
 (a) an amino acid sequence selected from the group consisting of SEQ ID Nos: 13 to 19 and 27 to 34; and/or
 (b) a neoantigen having an amino acid sequence selected from the group consisting of SEQ ID Nos: 13 to 19 and 27 to 34; and/or
 (c) an amino acid sequence having less than 100% sequence identity or similarity to the native HLA-A antigen peptide, such as at least 85%, more preferably at least 90% sequence identity (as defined herein) to an amino acid sequence selected from the group consisting of SEQ ID Nos: 1 to 5, 13 to 19 and 27 to 34; and/or
 (d) an amino acid sequence comprising or consisting essentially of only one amino acid substitution relative to the amino acid sequence(s) selected from the group consisting of SEQ ID NOs: 1 to 5, 13 to 19, and 27 to 34; and/or
 (e) Compounds, constructs, proteins or polypeptides consisting of at least two identical or different peptide sequences of at least one HLA-A tumor antigen peptide and one HLA-A, HLA-B and/or HLA-C tumor antigen peptide and/or corresponding neoantigens thereof, in which the HLA antigen peptides are optionally connected to each other by suitable linkers (so-called oligopeptides).

Very preferably, HLA-A tumor antigen peptides are as defined in (b), (d) and (e), respectively. Also in the embodiment according to (e), the HLA-A tumor antigen peptides are preferably defined as described under (a) or (d), respectively. In the case that the HLA-A tumor antigen peptides and/or neoantigens as defined under (e) are linked to each other via a linker, suitable linkers are known to the skilled person from the prior art.

The use of compounds, constructs, proteins or polypeptides as defined under (e) according to the invention, which consist of at least two identical or different peptide sequences of HLA tumor antigen peptides and/or HLA neoantigens, has the further advantage that the longer amino acid sequences of the compounds, constructs, proteins or polypeptides result in a longer retention time in the tissue of the subject after application, whereby the compounds, constructs, proteins or polypeptides after application to the subject can be broken down, for example, by the body's own enzymes into smaller fragments (pharmaceutically active form comprising at least 7 to 11 amino acids) which have a biologically desired function in the sense of the invention. by endogenous enzymes into smaller fragments (pharmaceutically active form comprising at least 7 to 11 amino acids) which have a biologically desired function in the sense of the invention. That is, the individual fragments of the oligopeptide exhibit activity as HLA-A, HLA-B or HLA-C tumor antigen peptides and thus contribute to the activation of T cells.

In a particular embodiment, any HLA-A peptide sequence may be a humanized and/or sequence optimized sequence as further described herein.

B) HLA-B Antigen Peptides and HLA-B Neoantigen Peptides

An "HLA-B antigen peptide" is defined herein as an "HLA-B antigen peptide of the invention" or "amino acid sequence of the invention" (as defined herein) comprising:

a) an amino acid sequence consisting of 12 to 17 amino acids; and/or b) a neoantigen peptide with an amino acid sequence consisting of 12 to 17 amino acids, which is i) is analogous to at least one HLA-B antigen peptide exposed on the cell surface of cells from malignant and/or neoplastic tissue (in particular mammary/breast carcinoma) of the individual to be treated, and ii) in its amino acid sequence at least one amino acid exchange with the wild type of this HLA-B antigen peptide (so-called "HLA-B neoantigen peptide") and iii) has at least a 3-fold increased specific affinity towards the T cell receptor of endogenous T cells Furthermore, the inventors have recognized that HLA-B neoantigen peptides which in their amino acid sequence have at least one amino acid exchange in amino acid positions 3, 8 and/or 10 compared to the wild type of this HLA-B antigen peptide, have an at least 4-fold, particularly preferably at least 7-fold increased specific affinity towards the T cell receptor of the body's own T cells and are therefore particularly preferred for use in the formulation according to the invention.

Particularly preferably, the amino acid exchange in the amino acid sequence of the HLA-B antigen peptide is a single amino acid exchange in amino acid position 3, 8 or 10.

Preferably, the amino acid exchange in the amino acid sequence of the HLA-B neoantigen relative to the wild-type of this HLA-B antigen peptide is an E/A, E/K, R/W, or D/A exchange.

Preferably, the HLA-B antigen peptide or the HLA-B neoantigen peptide has a specific activity ($K_D$) towards the T cell receptor, as determined by any suitable detection method known to the skilled person in the prior art, of less than 100 nM, more preferably less than 75 nM or most preferably less than 50 nM, such as less than 40 nM, 35 nM, 30 nM, 25 nM or 20 nM.

Preferably, the HLA-B tumor antigen peptide or the HLA-B neoantigen is present in the pharmaceutical composition according to the invention at a concentration, as defined above, of at least 100 to 600 μg, alternatively preferably at an absolute concentration of >600 μg relative to the volume of the pharmaceutical composition to be applied.

Preferably, the HLA-B peptides or HLA-B neoantigens are selected as defined above under point b).

According to a particularly preferred embodiment, an "HLA-B neoantigen" is preferred, comprising the following scaffold sequence:

(a) an amino acid sequence selected from the group consisting of SEQ ID NO: 20, 21, 22 and 35; and/or (b) an amino acid sequence having at least 80%, such as at least 85%, more preferably at least 90%, sequence identity (as defined herein) with an amino acid sequence selected from the group consisting of SEQ ID Nos: 6, 7, 8, 20, 21, 22 and 35; and/or (c) an amino acid sequence comprising or consisting essentially of only one amino acid substitution relative to the amino acid sequence(s) selected from the group consisting of SEQ ID NOs: 6, 7, 8, 20, 21, 22 and 35; and/or (d) Compounds, constructs, proteins or polypeptides consisting of at least two identical or different peptide sequences of at least one HLA-B tumor antigen peptide and one HLA-A, HLA-B and/or HLA-C tumor antigen peptide and/or corresponding neoantigens thereof, in which the HLA antigen peptides are optionally connected to each other by suitable linkers (so-called oligopeptides).

Very preferably, HLA-B peptides are as defined in (a), (c) and (d), respectively. Also in the embodiment according to (d), the HLA-B peptides are preferably defined as described under (a) or (c). In the case that the HLA-B tumor antigen peptides and/or HLA-B neoantigens, as defined under (e), are linked to each other via a linker, suitable linkers are known to the person skilled in the art from the prior art.

The use of compounds, constructs, proteins or polypeptides as defined under (d) according to the invention, which consist of at least two identical or different peptide sequences of HLA tumor antigen peptides and/or HLA neoantigens, has the further advantage that the longer amino acid sequences of the compounds, constructs, proteins or polypeptides result in a longer retention time in the tissue of the subject after application, whereby the compounds, constructs, proteins or polypeptides can be broken down after application to the subject, for example, by the body's own enzymes into smaller fragments (pharmaceutically active form comprising at least 7 to 11 amino acids) which have a biologically desired function in the sense of the invention. That is, the individual fragments of the oligopeptide exhibit activity as HLA-A, HLA-B, or HLA-C tumor antigen peptides and thus contribute to T cell activation.

In a particular embodiment, any HLA-B peptide sequence may be a humanized and/or sequence optimized sequence as further described herein.

C) HLA-C Antigen Peptides and HLA-C Neoantigen Peptides

An "HLA-C antigen peptide" is defined herein as an "HLA antigen peptide of the invention" or "amino acid sequence of the invention" (as defined herein) comprising:

a) an amino acid sequence consisting of 8 to 11 amino acids; and/or b) a neoantigen peptide having an amino acid sequence consisting of 8 to 11 amino acids which is i) is analogous to at least one HLA-C antigen peptide exposed on the cell surface of cells from malignant and/or neoplastic tissue (in particular mammary/breast carcinoma) of the individual to be treated, and ii) in its amino acid sequence at least one amino acid exchange with the wild type of this HLA-C peptide (so-called "HLA-C neoantigen peptide") and iii) has at least a 3-fold increased specific affinity towards the T cell receptor of endogenous T cells Furthermore, the inventors have recognized that HLA-C neoantigen peptides which in their amino acid sequence compared to the wild type of this HLA-C antigen peptide have at least one amino acid exchange in the amino acid positions 1 (N-terminus), 4 and/or the C-terminus, have an at least 4-fold, particularly preferably at least 5-fold, very particularly preferably at least 7-fold increased specific affinity towards the T cell receptor of the body's own T cells and are therefore particularly preferably used for the formulation according to the invention.

Particularly preferably, the amino acid exchange in the amino acid sequence of the HLA-C antigen peptide is a single amino acid exchange in amino acid position 1 (N-terminus), 4 or the C-terminus.

Preferably, the amino acid exchange in the amino acid sequence of the HLA-C neoantigen peptide relative to the wild-type of this HLA-C antigen peptide is a C/Y, NP, L/F, or T/M exchange.

Preferably, the HLA-C antigen peptide or the HLA-C neoantigen peptide has a specific activity ($K_D$) towards the T cell receptor, as determined by any suitable detection method known to the skilled person in the prior art, of less than 100 nM, more preferably less than 75 nM or most preferably less than 50 nM, such as less than 40 nM, 35 nM, 30 nM, 25 nM, or 20 nM.

Preferably, the HLA-C tumor antigen peptide or the HLA-C neoantigen is present in the pharmaceutical composition according to the invention at a concentration, as defined above, of at least 100 to 600 µg, alternatively preferably at an absolute concentration of >600 µg relative to the volume of the pharmaceutical composition to be applied.

Preferably, the HLA-C antigen peptides or HLA-C neoantigen peptides are selected as defined above under point b).

According to a particularly preferred embodiment, an "HLA-C neoantigen peptide", is preferred, comprising the following scaffold sequence:

(a) an amino acid sequence selected from the group consisting of SEQ ID NOs: 23 to 26; and/or (b) an amino acid sequence having at least 80%, such as at least 85%, more preferably at least 90%, sequence identity (as defined herein) with an amino acid sequence selected from the group consisting of SEQ ID Nos: 9 to 12 and 23 to 26; and/or (c) an amino acid sequence comprising or consisting essentially of only one amino acid substitution relative to the amino acid sequence(s) selected from the group consisting of SEQ ID Nos: 9 to 12 and 23 to 26; and/or (d) Compounds, constructs, proteins or polypeptides consisting of at least two identical or different peptide sequences of at least one HLA-C tumor antigen peptide and one HLA-A, HLA-B and/or HLA-C tumor antigen peptide and/or corresponding neoantigens thereof, in which the HLA antigen peptides are optionally connected to each other by suitable linkers (so-called oligopeptides).

Very preferably, HLA-C peptides are as defined in (a), (c) and (d), respectively. Also in the embodiment according to (d), the HLA-C antigen peptides are preferably defined as described under (a) and (c), respectively. In the case that the HLA-C tumor antigen peptides and/or HLA-C neoantigens, as defined under (d), are linked to each other via a linker, suitable linkers are known to the person skilled in the art from the prior art.

The use of compounds, constructs, proteins or polypeptides as defined under (d) according to the invention, which consist of at least two identical or different peptide sequences of HLA tumor antigen peptides and/or HLA neoantigens, has the further advantage that the longer amino acid sequences of the compounds, constructs, proteins or polypeptides result in a longer retention time in the tissue of the subject after application, whereby the compounds, constructs, proteins or polypeptides after application to the subject can be broken down, for example, by the body's own enzymes into smaller fragments (pharmaceutically active form comprising at least 7 to 11 amino acids) which have a biologically desired function in the sense of the invention. I.e., the individual fragments of the oligopeptide exhibit an activity as HLA-A, HLA-B or HLA-C tumor antigen peptides and thus contribute to the activation of T cells.

In a particular embodiment, any HLA-C antigen peptide sequence may be a humanized and/or sequence optimized sequence as further described herein.

D) HLA Class II Antigen Peptides and HLA-II Neoantigen Peptides

An "HLA class II antigen peptide" is defined herein as an "HLA peptide of the invention" or "amino acid sequence of the invention" (as defined herein) comprising:

a) an amino acid sequence consisting of 13 to 20 amino acids, particularly preferably 13 to 17 amino acids; and/or b) a neoantigen having an amino acid sequence consisting of 13 to 20 amino acids, particularly preferably 13 to 17 amino acids, which is i) is analogous to at least one class II HLA peptide exposed on the cell surface of cells from malignant and/or neoplastic tissue (in particular mammary/breast carcinoma) of the individual to be treated, and ii) in its amino acid sequence at least one amino acid exchange compared to the wild type of this class II HLA peptide (so-called "class II HLA neoantigen") and iii) has at least a 3-fold increased specific affinity towards the T cell receptor of endogenous T cells Furthermore, the inventors have recognized that HLA neoantigens of class II, which in their amino acid sequence compared to the wild type of this HLA peptide of class II have at least one amino acid exchange in amino acid positions 3, 6, 10, 12, 13 and/or 14, particularly preferably in amino acid positions 12 and/or 14, have an at least 4-fold increased specific affinity towards the T cell receptor of the endogenous T cells and are therefore particularly preferred for use in the formulation according to the invention.

Particularly preferably, the amino acid substitution in the amino acid sequence of the class II HLA peptide is a single amino acid substitution at amino acid position 12 or 14.

Preferably, the amino acid exchange in the amino acid sequence of the class II HLA neoantigen relative to the wild-type of this class II HLA peptide is an E/K, E/A, D/Y, or T/M exchange.

Preferably, the class II HLA peptide or class II HLA neoantigen has a specific activity (KD) towards the T cell receptor, as determined by any suitable detection method known to the skilled person in the prior art, of less than 100 nM, more preferably less than 75 nM, or most preferably less than 50 nM, such as less than 40 nM, 35 nM, 30 nM, 25 nM or 20 nM.

Preferably, the HLA tumor antigen peptide corresponding to the MHC complexes of class II or the HLA neoantigen corresponding to the MHC complexes of class II is present in the pharmaceutical composition according to the invention at a concentration, as defined above, of at least 100 to 600 µg, alternatively preferably at an absolute concentration of >600 µg relative to the volume of the pharmaceutical composition to be administered.

Preferably, the class II HLA peptide(s) or class II HLA neoantigen(s) are selected as defined above in point b).

According to a particularly preferred embodiment, an "HLA class II neoantigen", is preferred, comprising the following scaffold sequence:

(a) an amino acid sequence selected from the group consisting of SEQ ID NOs: 36, 37, 38, 41, 42, 43, 44, 45, 46, 47, 48; and/or (b) a neoantigen having an amino acid sequence having at least 80%, such as at least 85%, more preferably at least 90%, sequence identity (as defined herein) with an amino acid sequence selected from the group consisting of SEQ ID NO: 36 to 48; and/or (c) a neoantigen having an amino acid sequence comprising or consisting essentially of only one amino acid substitution relative to the amino acid sequence(s) selected from the group consisting of SEQ ID NO: 36 to 48; and/or (d) compounds, constructs, proteins or polypeptides consisting of at least two identical or different class II HLA peptide sequences in which the class II HLA antigen peptides are linked together by suitable linkers (so-called oligopeptides).

(e) Compounds, constructs, proteins or polypeptides consisting of at least two identical or different peptide sequences of at least one HLA antigen peptide sequence of class II and one HLA antigen peptide sequence of class II, HLA-A, HLA-B and/or HLA-C antigen peptide sequence and/or corresponding neoantigens thereof, in which the HLA antigen peptides are optionally connected to each other by suitable linkers (so-called oligopeptides).

Very preferably, HLA antigen peptides of class II are as defined in (a), (c) and (d), respectively. Also in the embodiment according to (d), the HLA class II antigen peptides are preferably defined as described under (a) or (c), respectively. In the case that the HLA tumor antigen peptides of class II and/or corresponding neoantigens, as defined under (d), are linked to each other via a linker, suitable linkers are known to the person skilled in the art from the prior art.

The use of compounds, constructs, proteins or polypeptides as defined under (d) according to the invention, which consist of at least two identical or different peptide sequences of HLA tumor antigen peptides and/or HLA neoantigens, has the further advantage that the longer amino acid sequences of the compounds, constructs, proteins or polypeptides result in a longer retention time in the tissue of the subject after application, whereby the compounds, constructs, proteins or polypeptides after application to the subject can be broken down, for example, by the body's own enzymes into smaller fragments (pharmaceutically active form comprising at least 7 to 11 amino acids) which have a biologically desired function in the sense of the invention. I.e., the individual fragments of the oligopeptide exhibit an activity as HLA-A, HLA-B or HLA-C tumor antigen peptides and thus contribute to the activation of T cells.

In a particular embodiment, any class II HLA peptide sequence may be a humanized and/or sequence optimized sequence as described further herein.

The use of at least 2 HLA tumor antigen peptides of class II for the treatment of breast cancer according to the invention has the significant advantage that B cells are also activated in a targeted manner in the subject to be treated.

The use of HLA tumor antigen peptides of class II according to the invention has the further advantage that HLA antigen peptides, which have longer amino acid sequences than HLA tumor antigen peptides of class I, can be broken down after application to the test person, for example by the body's own enzymes, into smaller fragments (comprising at least 7 to 11 amino acids), which have an activity as HLA-A, HLA-B or HLA-C antigen peptides and thus contribute to the activation of T cells.

"Fragment" means a portion of a polypeptide that preferably contains at least 10%, 20%, 30%, 40%, 50%, 60%, 70%, 80%, 90%, 95% or more of the total length of the reference polypeptide. A fragment may contain 7, 8, 9, 10, 11 or more amino acids.

In particular, amino acid sequences and polypeptides of the invention are preferred as defined in the claims and those in which:

at least one HLA tumor antigen peptide is analogous to at least one HLA tumor antigen peptide exposed on the cell surface of cells from malignant and/or neoplastic tissue of the individual to be treated, which peptide has in its amino acid sequence at least one amino acid exchange compared to the wild type of said HLA tumor antigen peptide (i.e. HLA neoantigen peptide) and, compared to the wild type of this HLA tumor antigen peptide, has at least a 3-fold increased specific affinity towards the T cell receptor of the body's own T cells.

It is an outstanding achievement of the inventors to have found that a pharmaceutical composition comprising more than 3 such HLA tumor antigen peptides is particularly effective. Therefore, the pharmaceutical composition according to the invention preferably comprises at least six, very preferably at least eight, very particularly preferably ten of the aforementioned HLA tumor antigen peptides corresponding to MHC complexes of class I and/or II.

Preferably, a monovalent amino acid sequence (or a polypeptide comprising only one amino acid sequence of the invention) used in the invention is such a one as to bind to a T cell receptor of endogenous T cells with a 3-fold increased specific affinity compared to the corresponding wild-type HLA peptide sequence.

It should be noted that "may specifically bind to" and "specifically binds to" are used interchangeably herein and refer to the ability to specifically bind to the corresponding specified entity.

It is important in connection with the present invention that the diagnosis of the cancer(s) be made in advance by the attending physician.

It is possible to combine amino acid sequences belonging to different classes used in the invention in a single polypeptide of the invention. In particular, it has been demonstrated that the combination of HLA-A, HLA-B and/or HLA-C tumor antigen peptides and/or corresponding neoantigen peptides in a single polypeptide of the invention have unique binding properties (cf. FIG. 3).

By one skilled in the art, the specific activity (KD) of the polypeptides of the invention comprising more than one component of the amino acid sequence of the HLA-A, HLA-B and/or HLA-C tumor antigen peptides and/or neoantigen peptides corresponding to the MHC complexes of class I or II can be determined according to one of the detection methods described above/below, wherein the compounds, constructs, proteins or polypeptides of the invention preferably have a specific activity similar to the specific activity of each of their components, i.e. a specific activity similar to the specific activity of each of the (individual components of the) amino acid sequences of class I or II contained in the compounds, constructs, proteins or polypeptides of the invention. Some specific, but not limiting, examples of the above preferred compounds, constructs, proteins or polypeptides are compounds, constructs, proteins or polypeptides that either comprise i) a wild-type HLA tumor antigen peptide corresponding to class I MHC complexes (HLA-A, HLA-B, or HLA-C peptide, respectively) and/or II; or ii) a neoantigen corresponding to class I MHC complexes (HLA-A, HLA-B and HLA-C neoantigen, respectively) and/or II having an amino acid sequence selected from the group consisting of SEQ ID NO: 1 to 48; or iii) a neoantigen corresponding to class I MHC complexes (HLA-A, HLA-B and HLA-C neoantigen, respectively) and/or II having an amino acid sequence having at least 80% sequence identity (as defined herein) to an amino acid sequence selected from the group consisting of SEQ ID NO: 1 to 48; or iv) an amino acid sequence comprising or consisting essentially of only one amino acid substitution relative to the amino acid sequence selected from the group consisting of SEQ ID Nos: 1 to 48; or v) Compounds, constructs, proteins or polypeptides consisting of at least two identical or different HLA antigen peptide sequences, in which the HLA peptides are optionally connected to each other by suitable linkers; or comprise a suitable combination thereof.

Note that the last preceding paragraphs also apply generally to all amino acid sequences of the invention comprising one or more amino acid sequences for HLA tumor antigen peptides and/or HLA neoantigen peptides according to A), B), C) and D), respectively.

Of course, all of the above HLA tumor antigen peptides corresponding to class I and class II MHC complexes can be used and are effective for the treatment of a cancer as disclosed herein, particularly for the treatment of mammary/breast carcinomas.

Some specific, but not limiting, examples of such compounds, constructs, proteins or polypeptides of the invention are set forth, for example, in Tables 1–4 or are apparent to those skilled in the art based on the present disclosure.

According to another preferred embodiment of the present invention, the HLA tumor antigen peptide is present (in each case) as a single-membered amino acid sequence, i.e. not as an element of compounds, constructs, proteins or polypeptides consisting of at least two identical or different amino acid sequences for HLA tumor antigen peptides/neoantigens, in which the HLA tumor antigen peptides/neoantigens are connected to each other by suitable linkers.

Preferably, the HLA tumor antigen peptides of the invention exhibit specific activity towards T cell receptors (T cells are used for this purpose), which can be determined using any suitable detection method known to those skilled in the art, such as EliSpot AlphaScreen detection methods (as described herein) or cell-based detection methods (as described herein). Preferably, the blocking activity is determined using a cell-based detection method, such as described in embodiments 3 and 4

In particular, the compounds, constructs, proteins or polypeptides of the invention comprising an amino acid sequence of an HLA antigen peptide of the invention and belonging to MHC class I (as defined herein) preferably have a specific affinity of 10 to 50 nM towards the corresponding T cell receptor.

It is also within the scope of the present invention that an amino acid sequence of the invention can bind to two or more class I or class II MHC complexes, epitopes, components, domains or subunits of a class I or class II MHC complex. In such a case, the MHC complexes, epitopes, components, domains, or subunits of an MHC complex to which the amino acid sequences and/or polypeptides of the invention bind may be substantially the same or different (and in the latter case, the amino acid sequences and polypeptides of the invention may bind to such different complexes, epitopes, components, domains, or subunits of a class I or class II MHC complex, including combinations thereof, with an affinity and/or specificity that may be the same or different)

It is also expected that the polypeptides of the invention will generally bind to all naturally occurring or synthetic analogs, variants, mutants, components and fragments of a class I or class II MHC complex, respectively. Also in such a case, the amino acid sequences and polypeptides of the invention may bind to such analogs, variants, mutants, alleles, components and fragments with an affinity and/or specificity equal to or different from the affinity and specificity with which the amino acid sequences of the invention bind to the wild types of the class I or II MHC complex, respectively.

It is also within the scope of the present invention that the amino acid sequences and polypeptides of the invention bind to some analogs, variants or mutants of a class I or class II MHC complex, respectively, but do not bind to other.

In a specific, but not limiting, embodiment of the present invention, compounds, constructs, proteins or polypeptides comprising an HLA tumor antigen peptide of the invention may have an increased half-life in serum compared to the amino acid sequence from which they were derived. For example, an amino acid sequence of the present invention may be linked (chemically or otherwise) to one or more groups or moieties that extend half-life (such as PEG) such that they are a derivative of an amino acid sequence of the invention with increased half-life.

In general, the compounds or polypeptides of the invention with increased half-life preferably have a half-life that is at least 1.5 times, preferably at least 2 times, such as at least 5 times, for example at least 10 times or more than 20 times higher than the half-life of the corresponding amino acid sequence of the invention per se. For example, the compounds or polypeptides of the invention with increased half-life have a half-life that is more than 1 hour, preferably more than 2 hours, more preferably more than 6 hours, such as more than 12 hours or even more than 24, 48 or 72 hours higher compared to the corresponding amino acid sequence of the invention per se.

In general, when an HLA tumor antigen peptide of the invention (or a compound, construct or polypeptide comprising the same) is intended for administration to a patient (for example, for therapeutic and/or diagnostic purposes, as defined herein), it is preferably either an amino acid sequence that does not naturally occur in the patient; or, if naturally occurring in the patient, it is present in substantially isolated and simultaneously concentrated form (as defined herein).

In addition, it will also be apparent to those skilled in the art that, for pharmaceutical use, the HLA tumor antigen peptides of the invention (and the compounds, constructs and polypeptides comprising the same) will be directed against a human T cell receptor including combinations thereof as defined in the claims; wherein, for veterinary purposes, the polypeptides of the invention are preferentially directed against a T cell receptor including combinations thereof (as defined in the claims) from the species to be treated, or are at least cross-reactive towards a T cell receptor including combinations thereof from the species to be treated.

The mammary/breast cancer to be treated is preferably a hormone-positive, HER2/neu, or triple-negative breast cancer.

Method for the Determination/Identification of HLA Antigen Peptides

Also encompassed by the present invention is a method for determining pharmaceutically active HLA tumor antigen peptides for use in the treatment or prophylaxis of breast cancer or in a pharmaceutical composition according to the invention, said method comprising monitoring a tissue resection of a patient or group of patients suffering from or suspected of suffering from breast cancer, said method comprising the following steps:

(a) providing a tissue sample from a tissue resection, preferably of a mammary/breast carcinoma of the patient or group of patients, wherein the cells of the tissue sample express MHC complexes of class I and/or II and these are presented on their surface, wherein said method step (a) of providing the tissue sample itself does not comprise a surgical intervention in the patient or one of the patients of the group of patients, respectively;

(b) Determine the following parameters using the provided tissue sample of the tissue resection from step (a):

i) the transcriptome of the provided tissue sample to determine all DNA sequences transcribed into mRNA sequences and to quantify the mRNA sequences, and Compare the determined transcriptome with the transcriptome of a healthy tissue sample of the patient or patient group to determine up- and/or down-regulated mRNA sequences that deviate by a factor of 3 from the threshold value in the healthy tissue sample;

the specific HLA haplotype, preferably including the HLA haplosubtypes of the patient or group of patients, and most preferably with respect to the MHC class I complexes, and if applicable, deriving the preferred anchor positions of the MHC class I complexes (as defined herein);

ii) the exome sequence of the tissue sample provided to identify all DNA sequences potentially coding for proteins, and Comparison of the exome of the provided tissue sample with the exome of a healthy tissue sample or with a gene database (library) of the patient or patient group to determine somatic mutations, whereby germline mutations in healthy tissue are advantageously excluded so that an autoimmune response is prevented upon/after application of the determined HLA antigen peptides to the patient or patient group (obtaining a healthy tissue sample from the patient or patient group can be done, for example, by taking a blood sample with nucleated cells); and Determine the HLA tumor antigen peptides associated with proliferation, invasiveness, angiogenesis, and an increase in cytokeratin production of mammary/breast carcinoma; and Determine the HLA tumor antigen peptides associated with proliferation, invasiveness, angiogenesis, and an increase in cytokeratin production of a mammary/breast carcinoma;

iii) of the ligandome to determine the HLA tumor antigen peptides presented on the surface of the cells of the mammary/breast carcinoma determined in step (iii), optionally also determining the HLA antigen peptides presented on the surface of cells of a healthy tissue sample of the patient or patient group;

iv) the specific binding affinity of the HLA tumor antigen peptides determined in step (iv) towards the corresponding class I and/or class II MHC complex expressed in the cells of the tissue sample, preferably of a breast/mammary carcinoma, and presented on the surface of these cells, by means of a database and/or a ranking algorithm; and/or v) optionally the immunogenicity of the HLA tumor antigen peptides determined in step (iv) by means of an immunogenicity test in particular by Western blot, ELISA techniques in particular by ELISPOT, AFM or immunodetection with microscopic analysis;

(c) Selection of HLA tumor antigen peptides, preferably at least 4 to 8 HLA-A tumor antigen peptides corresponding to MHC class I complexes and at least 2 antigen peptides corresponding to MHC class II complexes, which meet the criteria according to the parameters defined in step (b) and which are expressed in the cells of the tissue sample provided and presented on the surface of these cells.

According to a preferred embodiment of the method for determining pharmaceutically active HLA tumor antigen peptides, immediately after providing the tissue sample of the patient or patient group in step (a), the BRCA1 and BRCA2 genes are examined for the presence of mutations.

Particularly preferably, determining whether the HLA tumor antigen peptides are presented on the surface of the cells of the tissue sample of the patient or group of patients provided in step a) is performed by ultra-high performance liquid chromatography (UHPCL) in conjunction with ESI mass spectrometry (MS).

According to a preferred embodiment, the method for determining a class I and/or class II HLA peptide in step (b) comprises generating a transcriptome of the tissue sample provided in step (a).

Preferably, the transcriptome is generated by RT-PCR, followed by DNA microarray or DNA sequencing.

Particularly preferably, the method for determining a class I and/or class II HLA antigen peptide in step (b) comprises generating an exome sequencing for said tissue sample provided in step (a).

It is also desirable that the method for determining a pharmaceutically active class I and/or class II HLA tumor antigen peptide in step (b) comprises matching the determined amino acid sequences of the HLA antigen peptides corresponding to the class I and/or class II MHC complexes with a set, collection, or library of amino acid sequences to rank in terms of protein quantity (i.e., factors associated with proliferation, invasiveness, angiogenesis, and/or an increase in cytokeratin production of mammary/breast carcinoma) and specific affinity towards the T cell receptor of endogenous T cells (content factors for tumor progression, such as invasiveness, angiogenesis, but also the escape mechanisms of the tumor towards immune attack)

The method also comprises matching the determined parameters with amino acid sequences of the HLA tumor antigen peptides with a series, collection, or library of amino acid sequences of healthy expression data for amino acid sequences that can bind to or have affinity for MHC class I complexes or MHC class II complexes, including combinations thereof, as determined in step (i).

In such a method, the series, collection, or library of amino acid sequences may be an appropriate series, collection, or library of amino acid sequences. For example, the series, collection, or library of amino acid sequences may be a series, collection, or library of class I and class II HLA tumor antigen peptides and/or MHC complexes (as described herein), such as a native series, collection, or library of class I and class II HLA tumor antigen peptides and/or MHC complexes; be a synthetic or semi-synthetic series, collection or library of class I and class II HLA tumor antigen peptides and/or MHC complexes and/or a series; be a collection or library of class I and class II HLA tumor antigen peptides and/or MHC complexes that have been subjected to affinity maturation.

In order to specify the pharmaceutical efficacy of the HLA tumor antigen peptides determined by the derived ranking and to prevent or minimize the risk of an autoimmune response in the subject by the administration of the determined HLA tumor antigen peptides an immunogenicity test, in particular by means of Western blot, ELISA techniques, in particular by means of ELISPOT, AFM or immunodetection with microscopic analysis, is carried out with the HLA tumor antigen peptides (pre)determined by the determination method according to the invention. Advantageously, in this manifestation of the method for determining at least one pharmaceutically active HLA tumor antigen peptide, the time-consuming and costly preparation of a transcriptome and exome sequencing for this tissue sample can be omitted.

The present invention also comprises a method for determining the regression, progression or occurrence of a mammary/breast cancer disease, comprising monitoring a tissue resection, in particular a mammary/breast tissue, of a patient who has or is suspected of having a breast cancer, the method comprising the following steps:

(a) Providing a tissue sample from a subject, wherein the cells of the tissue sample express HLA class I and/or class II complexes and present them on their cell surface;

(b) Determine multiple parameters from the provided tissue sample selected from the group consisting of
i) the concentration (expression level) of at least 4 to 8 HLA-A antigen peptides corresponding to MHC class I complexes and at least 2 antigen peptides corresponding to MHC class II complexes expressed in the cells of the provided tissue sample and presented on the cell surface of these cells; and
ii) the amino acid sequence of at least said 4 to 8 HLA-A antigen peptides and at least said 2 class II antigen peptides expressed in the cells of the tissue sample provided and presented on the cell surface of said cells; and
iii) the specific binding affinity of the HLA-A antigen peptides and the class II antigen peptides determined in step ii) towards the T cell receptor of the endogenous T cells; and
iv) optional immunogenicity of the determined HLA-A antigen peptides and class II antigen peptides by means of an immunogenicity test (e.g. by Western blot, ELISA techniques, in particular by ELISPOT or immunodetection with microscopic analysis);

(c) Matching the determined amino acid sequences of the HLA antigen peptides with a series, collection or library of amino acid sequences for amino acid sequences capable of binding to or having affinity for MHC class I complexes or MHC class II complexes, including combinations thereof, determined in step (i), respectively.

A further, in particular cost-reduced embodiment of the method according to the invention for determining at least one HLA tumor antigen peptide corresponding to the MHC complexes of class I and/or II for a pharmaceutical composition according to the invention provides that exclusively (i.e. without prior preparation of a transcriptome, exome sequencing) the HLA tumor antigen peptides of class I and/or II are determined the HLA tumor antigen peptides of class I and/or II are determined which are exposed on the cell surface of cells from malignant and/or neoplastic tissue of the individual to be treated (so-called determination of the ligandome).

The procedure here consists of the following steps:
a) Providing a tissue sample from a tissue resection of a subject who preferably has, or is suspected of having, locally recurrent breast/mammary carcinoma; and
b) Determining/selecting the HLA tumor antigen peptides exposed on the cell surface of the cells of the sampled tissue according to the determination of the parameters based on the provided tissue sample from step (a) according to step (b) of the aforementioned method for determining pharmaceutically active HLA tumor antigen peptides (as defined above); and
c) Determine the affinity of the HLA tumor antigen peptides exposed on the cell surface of the cells of the harvested tissue toward the T cell receptor of the endogenous T cells; and
d) Derive a ranking in terms of protein quantity (as specified herein) and specific affinity ($K_D$) towards the T cell receptors of the endogenous T cells;
wherein the sequence and/or combination of sequences is an HLA tumor antigen peptide corresponding to MHC class I complexes and/or MHC class II complexes or a combination of HLA tumor antigen peptides thereof and wherein the individual sequences are selected from the sequences of a database of nucleic acids.

Detailed Description and Definitions

In the present description and claims, the following terms are defined as follows:

In the context of the present invention, the features of the invention designated "comprising" are intended to be understood to include the more limited description of "consisting of" or "consisting essentially of" the same features of the present invention.

The term "and/or" is used to specifically disclose the two features or components together or separately. Therefore, the term "and/or" as used, for example, in the phrase "I and/or II" in the present disclosure includes "I and II," "I or II," "I" and "II".

A pharmaceutical composition is herein understood as a so-called informatic that can be administered to a patient or a group of patients having at least one identical HLA allele and that contains the combination of HLA tumor antigen peptides according to the invention in the concentration disclosed herein, wherein an HLA tumor antigen peptide represents an information carrier. This means that the arrangement of amino acids in the amino acid sequence of HLA tumor antigen peptides ("code") induces a sequence-specific activation of the immune system, in particular of T cells (by HLA tumor antigen peptides corresponding to MHC class I complexes) and/or B cells (by HLA tumor antigen peptides corresponding to MHC class II complexes). Thus, in vitro or in vivo loading of MHC class I complexes or MHC class II complexes of the tumor cells with the HLA tumor antigen peptides of the pharmaceutical composition according to the invention, which have an identical or slightly modified amino acid sequence with HLA tumor antigen peptides, or contacting T cells with said HLA tumor antigen peptides render tumor cells sensitive to lysis of the tumor cells of the tissue or tissue resection by specific cytotoxic or specifically activated T lymphocytes.

However, the primary objective of the present invention is not to load tumor cells with HLA tumor antigen peptides in vitro or in vivo, but to induce specific activation and training of the immune system, in particular of T cells and B cells against tumor cells. For this reason, the pharmaceutical composition according to the invention is preferably applied subcutaneously or intradermally and, preferably substantially simultaneously (i.e. successively) at least 2, particularly preferably at least 3 application sites, remote from a tumor lesion and/or the cancerous lymph node region. This has the particular advantage that the immune system or the T cells that recognize the applied HLA tumor antigen peptides process this information applied in the form of tumor antigen peptides and consequently specifically recognize and lyse tumor cells that present these HLA tumor antigen peptides on their surface.

Therefore, the method according to the invention has the advantage that in case the signals emitted by the tumor towards the immune system are too weak (passive) or the tumor actively secretes substances that promote its growth (stimulate macrophages) (active e.g. TREX or BD1 ramp up), the immune system, in particular the T cells can be trained to the presence of the tumor even if the signals emitted by the tumor are too weak. The signals emitted by the tumor are too weak when the presentation of HLA antigen peptides on the cell surface of the tumor cells is low or decreases in response to cytotoxic T cell attacks that have occurred (escapemechanism).

For the purposes of the present invention, an HLA antigen peptide is an HLA tumor antigen peptide if this is a tumor-exclusive HLA antigen peptide (i.e., expressed and/or exposed exclusively by tumor cells; a cancer testis antigen (CTA) that no longer occurs in the healthy/normal tissue of the adult patient/group of patients or a so-called neoantigen peptide) or a tumor-associated HLA antigen peptide.

"Tumor-exclusive HLA antigen peptides" are mutated HLA antigen peptides resulting, for example, from a mutation of a gene, where the mutation of the gene is causative for tumor growth and/or is related to oncogenesis. The mutated gene product in the tumor is specific for the individual patient or a certain group of patients with at least one identical HLA allele.

"Tumor-associated HLA antigen peptides" include non-mutated HLA antigen peptides expressed in the adult stage only in some tissues of the patient or a specific group of patients with at least one identical HLA allele, but also in tumor cells. The immunogenicity of tumor-associated HLA antigen peptides is usually low, since their presence in healthy cells can produce immunological tolerance (immune tolerance). Nevertheless, the induction of a strong immune response against HLA antigen peptides that are merely tumor-associated carries the risk of an autoimmune response.

Ein immunogenes HLA Tumorantigenpeptid wird hierin auch als "Epitop" bezeichnet.

According to a preferred embodiment of the present invention, MHC complexes corresponding to tumor-associated HLA antigen peptides are associated with proliferation, invasiveness, angiogenesis, and an increase in cytokeratin production of mammary/breast carcinoma. The skilled person is familiar with relevant databases and literature listing these effects (e.g., the National Center for Biotechnology Information (NCBI) databases).

The at least one HLA tumor antigen peptide within the scope of the present invention is particularly formulated for subcutaneous administration. The expression/term "composition" therefore means the provision of at least one HLA tumor antigen peptide and an adjuvant in a pharmaceutical formulation that allows good applicability and includes solutions, in particular injection solutions and infusion solutions, concentrates for the preparation of injection and infusion preparations, powders for the preparation of injection and infusion preparations and subcutaneous implants.

Pharmaceutical compositions are prepared by dissolving or suspending the determined HLA tumor antigen peptides in a carrier liquid (i.e., a pharmacologically acceptable vehicle), optionally with the addition of other excipients such as wetting agents, dyes, permeation enhancers, resorption enhancers, preservatives, antioxidants, light stabilizers.

The carrier fluid is preferably selected from the group consisting of sodium chloride injection solution, Ringers injection solution, isotonic dextrose, sterile water, dextrose solution, lactated Ringers injection solution, distilled water, or mixtures thereof, for local injection.

It is particularly advantageous for good solubility of the determined HLA tumor antigen peptides if their amino acid sequence has the lowest possible number of hydrophobic amino acids.

Preferably, dimethyl sulfoxide (DMSO), ethoxyethylene diglycol, ethanol, phosphatidylcholines, propylene glycol dipelargonates (DPPG), or glycolysed ethoxylated glycerides are suitable permeation promoters.

According to a preferred embodiment of the present invention, the pharmaceutical composition comprises water, a pharmaceutically acceptable saline solution and/or DMSO. For example, suitable pharmaceutical compositions for application include a mixture of about 30% DMSO and 70% water.

The term "class I HLA tumor antigen peptide (corresponding to MHC complexes)" as used herein refers to a peptide sequence that is bound to or immunogenic for the class I MHC complex (HLA complex in humans). The class I HLA protein complex is used for antigen presentation on the cell surface and comprises a heavy chain with 3 domains ($\alpha 1$, $\alpha 2$, and $\alpha 3$) and the $\beta 2$-microglobulin ($\beta 2M$).

The term "class II HLA tumor antigen peptide (corresponding to MHC complexes)" refers to a polypeptide sequence that is bound or immunogenic to the class II MHC complex (in humans, the HLA complex). The class II HLA protein complex is used for antigen presentation on the cell surface and consists of two chains of nearly equal size, an $\alpha$-chain and a non-covalently bound $\beta$-chain, each chain having two extracellular domains ($\alpha 1$ and $\alpha 2$ and $\beta 1$ and $\beta 2$).

As such, the polypeptides and pharmaceutical compositions of the present invention (as defined herein) may be used for use in the prevention and treatment of breast cancer (also referred to herein as "cancer of the invention"). In general, the "cancer of the invention" may be defined as diseases and disorders that can be appropriately prevented and/or treated by appropriate administration of either a tumor antigen peptide or a pharmaceutical composition of the invention (and, more particularly, a pharmaceutically effective amount thereof) to a subject (i.e., a person having the disease or disorder, or at least one symptom thereof, and/or who is at risk of contracting or developing such disease or disorder).

For the purposes of the present invention, a "peptide sequence" (e.g., an HLA antigen peptide) having a "native sequence" comprises a peptide sequence having the same (i.e., unmodified) amino acid sequence as a naturally occurring peptide sequence in the patient. Such a peptide sequence with a "native sequence" can be isolated from nature or produced recombinantly or synthetically. In particular, the term peptide sequence having a "native sequence" includes naturally occurring truncated or secreted forms of the peptide sequence (e.g., an extracellular domain sequence), naturally occurring variants (e.g., alternatively spliced forms), and naturally occurring allelic variants of the peptide sequence.

As further described herein, the amino acid sequences used in the invention are single variable HLA antigen peptide domains ("HLAs" or "HLA complex"). A single variable HLA antigen peptide domain is (as further defined herein) a region within the amino acid sequence of a protein that can be distinguished from its surrounding sequence on the basis of defined properties.

Amino acid sequences or regions within the amino acid sequence of a protein of the invention that are HLAs are also referred to herein as "HLAs of the invention." Some preferred examples of single variable HLA antigen peptide domains suitable for use in the invention are apparent from the further description herein and include, in particular, HLA-A, HLA-B and HLA-C antigen peptides corresponding to MHC class I complexes and HLA-DR, DQ and DP antigen peptides corresponding to MHC class II complexes.

Such neoantigen peptides (i.e., HLA antigen peptides expressed and/or exposed exclusively by tumor cells), which have less than 100% sequence identity or similarity to the native HLA antigen peptide, are preferably characterized in terms of the present invention by an amino acid substitution in the amino acid sequence.

The following terms are used to describe the sequence relationships between two or more amino acid sequences or polypeptide sequences: "reference sequence," "amino acid exchange," "sequence identity," "percentage of sequence identity," and "substantial identity".

In the context of the present invention, the term "amino acid substitution" refers to the substitution of one amino acid for another amino acid within the amino acid sequence of the HLA antigen peptide to be synthesized relative to the wild type of such HLA antigen peptide (i.e., native HLA antigen peptide). "Sequence identity," "percentage of sequence identity," or identity or similarity with respect to such amino acid sequence is defined herein as the percentage of amino acid residues in the amino acid sequence of the polypeptide that is identical (i.e., same residue) or similar (i.e., amino acid residue from the same group based on common side chain characteristics, see below) to the amino acid sequence of the wild type.

According to a preferred embodiment of the present invention, the amino acid exchange for the HLA antigen peptide corresponding to class I and/or class II MHC complexes comprises at least one of a D/Y, a C/Y, an NV, a T/M, an E/A, or a D/A exchange at any position within the amino acid sequence relative to the wild type of said HLA peptide.

The amino acids used herein are abbreviated according to the generally accepted single letter code of the IUPAC Nomenclature Commission. Where two amino acids are separated by a hyphen (/), this indicates that at a specific amino acid position in the amino acid sequence concerned, the wild-type amino acid (left side of the hyphen) has been replaced by another amino acid (right side of the hyphen).

To determine/derive preferred anchor positions and a preferred specific amino acid exchange in the amino acid sequence of HLA tumor antigen peptides, in silico modeling methods are particularly suitable, such as by means of the algorithm NetMHC 4.0 (http://www.cbs.dtu.dk/services/NetMHC/) based on the publications by Andreatta and Nielsen (Bioinformatics (2016) Feb. 15; 32(4):511-7) and Nielsen et al. (Protein Sci., (2003) 12:1007-17).

For purposes of comparing two or more amino acid sequences, the percentage of "sequence identity" between a first amino acid sequence and a second amino acid sequence may be calculated or determined by dividing the number of amino acids in the first amino acid sequence that are identical to amino acids at corresponding positions in the second amino acid sequence, by [the total number of amino acids in the first amino acid sequence] and multiplying by [100%], wherein each deletion, insertion, substitution or addition of an amino acid in the second amino acid sequence—compared to the first amino acid sequence—is considered as a difference to a single amino acid (position).

An HLA tumor antigen peptide is "immunogenic" if the tumor cells expose on their cell surface at least one corresponding MHC class I complex and/or at least one corresponding MHC class II complex that recognizes and binds to the HLA tumor antigen peptide, i.e. the HLA tumor antigen peptide exhibits a high specific activity towards this MHC class I complex and/or MHC class II complex. The immunogenicity of the HLA tumor antigen peptide can be determined by Western blot, ELISA techniques, in particular by ELISPOT or immunodetection with microscopic analysis.

The HLA tumor antigen peptides of the present invention are preferentially immunogenic and are therefore also referred to as immunogenic HLA tumor antigen peptides ("epitopes"). The immunogenicity of the HLA tumor antigen peptides can be determined by suitable detection methods. Such methods are known to the skilled person and/or described herein.

The term "specific affinity" or "specific binding affinity" of the HLA antigen peptide towards the T cell receptor (TCR) refers to the specific and reversible binding of the HLA peptide to the TCR of the endogenous T cells. This "specific affinity" according to the present invention is expressed in moles via the dissociation constant ($K_D$) determined by ligand binding assays.

Alternatively, the "specific affinity" of the HLA antigen peptide can also be determined by in silico methods.

According to a preferred embodiment of the present invention, at least one HLA-A tumor antigen peptide is a tumor-exclusive HLA-A tumor antigen peptide (i.e., a cancer testis antigen (CTA) that is no longer present in the healthy/normal tissue of the patient/group of patients or a so-called neoantigen peptide), and wherein the specific binding affinity of the tumor-exclusive HLA-A tumor antigen peptide is determined against the corresponding MHC class I complex with a $K_D$ in the range of 10 to 50 nM, as determined by surface plasmon resonance.

Based on conventional in silico binding prediction models (modeling), tumor antigen peptides with a $K_D$ of <50 nM are generally considered strong-binding and those with a $K_D$ between 50 and 500 nM are considered weak-binding tumor antigen peptides. However, in the in vivo determinations according to the invention, it has now been shown that the $K_D$ value is not necessarily important. Surprisingly, it was found that tumor antigen peptides that had a $K_D$ value in the range of 50 to 500 nM triggered effector cells (i.e., cytotoxic T cells) contrary to conventional in silico binding prediction models that considered them to have low binding. Thus, for tumor antigen peptide efficacy, it is essential that the tumor antigen peptides are immunogenic.

The term "active substance enhancer/adjuvant" refers to an adjuvant that triggers and/or enhances the effect of the HLA peptides in the first place. In principle, all commonly used adjuvants known to the skilled person are suitable for the production of a formulation according to the invention. However, the use of Montanide ISA 51 VG has proven to be particularly suitable. After application of the (drug) formulation to the test person, this forms a so-called granuloma which advantageously stores the HLA peptides in the form of a reservoir at the site of application and releases them into the organism of the test person over a longer period of time. Particularly advantageously, therefore, weekly applications of the (drug) formulation according to the invention are omitted. Preferably, the application of the (drug) formulation for the treatment of cancer diseases in the sense of the invention, when used over a longer period of time, therefore only has to be carried out every 2 weeks, particularly preferably only once a month.

The term "individual" (also referred to herein as "subject" or "patient") is used interchangeably with the term "subject" to mean any mammal that is being treated for an abnormal physiological condition or has been diagnosed with a disease.

The terms "individual" and "subject" as used in the present invention include mammals, such as a rodent, a carnivore, a cloven-hoofed animal, an odd-toed ungulate, or a primate. In particularly preferred embodiments, the subject is a human being.

Where reference is made herein to a "patient group", reference is always made to a group of individuals, preferably humans, who all have at least one, preferably at least two, most preferably at least three identical HLA allele(s).

It is permissible that patients to be treated with the pharmaceutical composition have received a standard therapy procedure (e.g., at least one surgery, radiation, chemotherapy, and/or hormone therapy).

However, the pharmaceutical composition may also be administered as a first-line therapy to the patient or specifically identified group of patients with at least one identical HLA allele.

According to a preferred embodiment of the present invention, the individual has not yet received chemotherapy for locally recurrent or metastatic breast cancer and/or has not received prior adjuvant chemotherapy in recurrence for 12 months or less since the last dose.

Particularly preferably, the individual has the haplotype with subgroup A*01 or A*02.

A "haplotype" (an abbreviation for "haploid genotype") is the sum of the composition of all specific alleles (=specific fingerprint) of a subject and denotes a variant of a nucleotide sequence on one and the same chromosome in the genome of a living being. A specific haplotype can be individual-, population- or even species-specific.

For the purposes of this invention, the transcriptome comprises the sum of all genes transcribed in a cell at a given time, i.e. transcribed from the DNA sequence into mRNA sequences, i.e. the totality of all as well as the quantification of the individual mRNA molecules produced in a cell. However, the creation of the transcriptome does not yet allow any statement about the "correctness" of the transcribed mRNA sequence.

In this context, the term "building a transcriptome" as used in the present disclosure refers to the analysis of the transcriptome as the sum of all genes transcribed in a cell at a given time point preferably by quantitative real-time (RT)-PCR followed by DNA microarray or subsequent DNA sequencing. Typically, constructing the transcriptome of the tissue sample provided in step (a) of the determination procedure of the invention comprises acquiring more than 40,000 coding DNA sequences (raw data).

In genetics, the exome is the totality of the exons of an organism, i.e. all sections that potentially code for proteins. In humans, the exome comprises about 23,000 genes with approximately 50 million nucleobases. Whole exome sequencing (WES) examines all exons, i.e. the sections coding for proteins in the genome of a tissue section (i.e. healthy tissue or tumor tissue of a test person). Genetic diagnostics focuses on these 1-2% of the human genome, where 85% of known disease-causing mutations are found.

Accordingly, exome analysis involves sequencing the exome of the patient (and other relatives, if applicable), evaluating the sequence data, and summarizing the results in a medical report. This diagnostic procedure is the method of choice to find the cause of the disease, especially in patients with complex or unspecific symptoms and a diagnosis that has often remained unexplained for years.

Compared to Whole Exome Sequencing (WES), in which all protein-coding regions of the approximately 23,000 known genes are enriched and sequenced, Clinical Exome Sequencing (CES) enriches a subset of the exome. In WES, the focus is on determining disease-associated genes described in the Human Gene Mutation Database (HGMD).

For the purposes of the present invention, the proteome refers to the totality of all proteins of at least one cell in a malignant or neoplastic tissue/tissue section or a cell compartment thereof, under precisely defined conditions and at a specific time. The proteome of a cell can be determined by proteome sequencing and is linked to the genome of that cell via the transcriptome.

Immunotherapies are based on deciphering the individual mutation pattern (signature) of the tumor of each cancer patient. Based on the profile of the mutation pattern, synthetic vaccines, for example RNA-based vaccines, are produced for each individual patient according to conventional treatment approaches (i.e. vaccine production or production of the informaticum according to the invention). These are subsequently used for the individual treatment of the patient.

Basically, these novel vaccines are not suitable for other patients with the same tumor, but can only be used for the respective patient whose mutanoma has been previously analyzed for vaccine production or production of the informaticum of the invention. Therefore, it is an outstanding achievement of the inventors to have recognized that different patients have overlap in the mutanoma of the malignant or neoplastic tissue/tissue resection thereof. Advantageously, different patients can be divided into uniform patient groups such that at least 50% of the HLA peptides of the formulation according to the invention is compatible with the mutanoma of the patient group.

The totality of all HLA antigen peptides presented on the cell surface via MHC molecules is referred to as the (HLA) ligandome for the purposes of the invention. It is believed that more than 105 HLA molecules are expressed on the cell surface and the number of identical HLA peptides presented can vary from a few to up to 10,000 copies per cell. Consequently, approximately 10,000 different HLA peptides are presented on a cell in varying proportions.

The ligandome is influenced by various physiological, intrinsic as well as pathological (e.g. cancer or necrosis) factors such as cell type or tissue type, infection or transformation of the cell, or simply the current state of the cell, which depends on nutrient situation or external stress factors, resulting in changes in the HLA peptides presented.

At the beginning of the analysis of the HLA ligandome, for example, Edman degradation can be used to gain first insights into the presented peptides. On the one hand, it is possible in this way to determine the general peptide motif of an allele via pool sequencing, and on the other hand, individual peptide sequences can already be determined via the analysis of individual reversed phase high performance liquid chromatography (RP-HPLC) fractions.

Alternatively or complementarily, the analysis of the ligandome can be performed by using modern mass spectrometers in proteomics, with which it is possible to unambiguously determine the sequences of many individual ligands. Two methods are used for the ionization of the peptides or proteins required for this purpose: Electrospray ionization (ESI) and matrix-assisted laser desorption/ionization (MALDI). In ESI, coupling with an RP-HPLC system is common. However, as the sensitivity of mass spectrometers has increased, capillary electrophoresis (CE) has also been used as an analytical separation method.

In order to achieve a higher sample throughput and increased sensitivity in ligandome analysis, the so-called UHPLC systems (ultra high performance liquid chromatography) can be used. These HPLC systems use only 2 µm diameter materials as packing material for separation columns, which leads to improved speed, efficiency and chromatographic separation.

In ESI mass spectrometry, the direct coupling of HPLC and ESI interface allows online separation of the sample, which, in combination with an autosampler, enables a fully automated measurement procedure. Because of the continuous solvent flow from the HPLC, samples can be measured in a relatively short time. ESI mass spectrometry uses a wide range of instruments for analysis such as quadrupole time-of-flight mass spectrometers, linear quadrupole ion traps, triple quadrupoles or ion trap-orbitrap hybrid systems. This advantageously allows the identification of hundreds of HLA peptides in one measurement.

The term "deriving a ranking" in the context of the present invention refers to determining/selecting the quantity and affinity of HLA peptides exposed on the cell surface of the cells of the harvested tissue (or a tissue section thereof).

Using the previous analyses, a cumulative ranking for the HLA antigen peptides with respect to protein quality and specific affinity ($K_D$) towards the T cell receptor of the endogenous T cells is derived. Thereby, with regard to protein quality, especially content-related factors for tumor progression, such as invasiveness, angiogenesis, but also the escape mechanisms of the tumor against the immune attack are evaluated.

A cumulative ranking system is used by the algorithm.

A cumulative (predictive) ranking is used to eliminate sequences.

In another embodiment, the highest-ranked sequence possibilities may be further qualified by their existence in a database of possible HLA antigen peptides with a high specific affinity to the endogenous T cell receptors (as defined herein) predicted from sequence data, particularly one that is restricted to the organism/proband from which the HLA antigen peptide was obtained. In another embodiment, the highest ranked sequence possibilities may be further qualified by the separation coordinates of the HLA antigen peptide (e.g., isoelectric point and molecular weight of a protein) and/or the monomer composition thereof.

To provide (tumor) antigen peptides, synthetic or isolated HLA tumor antigen peptides derived from the cumulative ranking can in principle be used for the preparation of the (drug) formulations of the present invention and for the preparation of the pharmaceutical composition (as so-called informatic).

However, it is a good idea to use synthetic HLA peptides. Processes for the synthetic production of peptides are known to the skilled person. Examples of such production methods are the Merrifield solid-phase peptide synthesis, the Bailey peptide synthesis and the N-carboxylic anhydride method.

A further object of the present invention is also (pharmaceutical) formulations in different dosage forms which contain the combination of active ingredients according to the invention and optionally further active ingredients and/or excipients.

Preferred drug formulations are tablets, chewable tablets, chewing gums, coated tablets, capsules, drops, juices, syrups, suppositories, transmucal therapeutic systems, transdermal therapeutic systems, solutions, injections, emulsions, suspensions, easily reconstitutable dry preparations, powders or sprays. Particularly preferred drug formulations are injections or solutions.

Alternatively, the drug formulation is present in a suitable application device, preferably as a lyophilizate in a syringe, which allows in situ reconstitution with a pharmaceutically acceptable solution (e.g., saline).

Preferably, the (drug) formulations according to the invention are suitable for oral, intravenous, intramuscular, subcutaneous, intrathecal, epidural, buccal, sublingual, pulmonary, rectal, transdermal, nasal or intracerebroventricular administration, with (drug) formulations for subcutaneous or intravenous administration being especially preferred.

Methods known in the prior art for the preparation of pharmaceutical compositions or dosage forms are found in, for example, "Remington's Pharmaceutical Sciences". Pharmaceutical compositions for parenteral administration may contain, for example, excipients, sterile water, or saline, polyalkylene glycols, such as polyethylene glycols, oils of vegetable origin, or hydrogenated naphthalenes. Biocompatible, biodegradable lactide polymer, lactide/glycolide copolymers, or polyoxyethylene-polyoxypropylene copolymers can be used to control the release of the compounds. Other potentially useful parenteral delivery systems for the therapeutic anti-prion compounds include ethylene vinyl acetate copolymer particles, osmotic pumps, implantable infusion systems, and liposomes.

Content Factors for Tumor Progression

Also important for establishing the ranking is the identification of factors that play a significant role in tumor progression (i.e. tumor size increase and/or metastasis). Characteristic of tumor progression are increased growth rate, as well as increased invasiveness of the tumor.

Invasiveness refers to the extent of tissue-penetrating growth of a malignant tumor from its site of origin into adjacent tissue structures.

Angiogenesis describes the emergence of new blood vessels from an already existing vascular system and is a component of both physiological processes (e.g. embryogenesis, wound healing) and pathological processes (e.g. diabetic retinopathy, chronic polyarthritis, tumor growth). It has been known for a long time that new vessel formation (angiogenesis) occurs in cancer, which is referred to as tumor angiogenesis. Tumors are composed of cells that, like all other cells in the body, require nutrients and oxygen. In fact, because cancer cells divide frequently, their need is particularly high. And that is why a tumor needs its own blood vessels.

When a tumor develops, it initially does not yet have its own blood vessels. Its growth is therefore severely restricted. Without its own blood vessels, it does not grow larger than 1 to 2 millimeters. The formation of metastases also interacts with tumor angiogenesis, because tumor cells must reach surrounding blood vessels to do so. Only then can they be transported to distant regions of the body and form metastases there.

For example, it is known that there is an interdependence between class I HLA and integrin β to stimulate signal transduction and cell proliferation. In this regard, integrin β-mediated cell migration depends on its interaction with class I HLA molecules (Zhang and Reed, Hum Immunol. 2012 December, 73(12), 1239-1244).

An HLA peptide of the invention, or a composition or formulation containing the same, may be used for modulating a class I or class II HLA complex, including combinations thereof, either in vitro (e.g., in an in vitro or cellular detection method) or in vivo (e.g. in a unicellular organism or in a multicellular organism and in particular in a mammal and more particularly in a human being, such as a human being at risk of developing, or suffering from, a cancer of the invention).

In the context of the present invention, "modulation" or "modulating" substantially means increasing the specific affinity of T cell toward a tumor-exclusive or tumor-associated MHC class I complex or MHC class II complex, respectively, of the malignant and/or neoplastic tissue, as measured by an appropriate in vitro, cellular, or in vivo detection method (such as those referred to herein). In particular, "modulating" or "modulate" means increasing the specific affinity of endogenous T cells of the patient or group of patients towards a tumor-exclusive or tumor-associated MHC class I complex or MHC class II complex of the malignant and/or neoplastic tissue, by at least 1%, preferably at least 5%, such as 10% or at least 25%, for example by at least 50%, at least 60%, at least 70%, at least 80% or 90% or more compared to the affinity of T cells towards a tumor-exclusive or tumor-associated MHC class I complex or MHC class II complex of the malignant and/or neoplastic tissue in the same detection method under the same conditions but without the presence or prior application of the HLA tumor antigen peptides of the pharmaceutical composition of the invention (as defined herein).

In a particular embodiment, the invention comprises the above method, wherein the expression profile of at least five, preferably at least six, most preferably at least 6 marker genes, as shown in SEQ ID NO: 1 to SEQ ID NO: 48, is determined. As mentioned above, the marker genes are also defined by variants, again shown in Tables 2 to 4. Preferably, this expression profile is compared to the expression profile of a "reference". For example, a reference can be the expression profile of healthy tissue (e.g., intestinal tissue or tissue of the liver, lung, etc.). Tissue of the affected individual (proband) can be used as "healthy tissue" in this context, whereby this tissue is known not to be proliferatively altered or even metastatic. Appropriate examples are shown in the experimental part of the invention. However, data from tissues of foreign individuals, preferably healthy individuals, can also be used as a "reference" or "reference value".

As set forth herein, according to the invention, in the method for the detection of a carcinoma, at least 6, but preferably at least 8, and most preferably at least 10 of the HLA antigen peptides shown herein corresponding to MHC class I complexes or MHC class I complexes (selected from the group of polypeptides/polypeptide segments as shown in SEQ ID Nos: 1 to 48) are to be determined. For further embodiments, please refer to the experimental section.

The present invention further comprises a process for the preparation of a pharmaceutical composition or (drug)formulation according to the invention, wherein the process comprises the following steps:

(a) Determining at least 4 to 8 HLA-A tumor antigen peptides corresponding to MHC class I complexes and at least 2 tumor antigen peptides corresponding to MHC class II complexes exposed on the cell surface of cells from a mammary/breast carcinoma of the patient to be treated or group of patients having the same haplotype by the determination method according to the invention as described above;

(b) synthesizing the 4 to 8 HLA-A tumor antigen peptides corresponding to MHC class I complexes and at least 2 tumor antigen peptides corresponding to MHC class II complexes determined in step (a), wherein the definition of each HLA tumor antigen peptide is the same as defined above; and (c) Preparing the pharmaceutical composition according to the invention comprising at least the 4 to 8 HLA-A tumor antigen peptides corresponding to the MHC class I complexes synthesized in step (b), the at least 2 tumor antigen peptides corresponding to the MHC class II complexes and an adjuvant as herein defined.

The present invention also comprises the use of the pharmaceutical composition or (drug)formulation according to the invention for the manufacture of a medicament or a combination preparation for the treatment of malignancies, leukemias and neoplasms, in particular breast cancer.

Also encompassed by the invention is a pharmaceutical composition comprising an HLA peptide as defined in the invention and a pharmaceutically acceptable excipient.

The invention also relates to an HLA antigen peptide or a neoantigen peptide of the invention for use in the preparation of a formulation (such as, without limitation, a pharmaceutical formulation, as further described herein) for the treatment of cancer, either in vitro (e.g. in an in vitro or cellular detection method) or in vivo (such as, for example, in a unicellular or multicellular organism and in particular in a mammal and more particularly in a human being, such as, for example, a human being at risk of developing or suffering from a cancer of the inventions).

The present invention further comprises a combination preparation for use in the treatment of mammary/breast carcinoma with simultaneous, separate, or sequential administration, the combination preparation comprises the following two separate preparations (a) and (b):

(a) a first preparation comprising, together with a pharmaceutically acceptable carrier or diluent, 4 to 8 HLA-A tumor antigen peptides corresponding to MHC class I complexes and at least 2 tumor antigen peptides corresponding to MHC class II complexes as described herein, and optionally determined by the method of the invention, and (b) a second preparation comprising, together with a pharmaceutically acceptable carrier or diluent, an anticancer agent selected from the group consisting of anticancer alkylating agents, anticancer antimetabolites, anticancer antibiotics, herbal anticancer drugs, platinum-coordinated anticancer complex compounds, anticancer camptothecin derivatives, anticancer tyrosine kinase inhibitors, monoclonal antibodies, interferons, interleukins, biological response modifiers, and other anticancer agents, or a pharmaceutically acceptable salt thereof.

The combination preparation according to the invention is particularly suitable for use in the treatment or prophylaxis of breast carcinomas, in particular locally recurrent or metastatic breast carcinomas, in a patient or group of patients suffering from or suspected of suffering from a breast carcinoma.

Particularly preferably, the first preparation of the combination preparation according to the invention is thereby administered subcutaneously.

Particularly good experience has been made in the administration of the pharmaceutical composition according to the invention (first preparation) in combination with the administration of herbal anticancer drugs, in particular artesunate and/or curcumin as the second preparation.

Nevertheless preferred is the combined administration of the pharmaceutical composition according to the invention (first preparation) in combination with a monoclonal antibody, in particular against immunosuppressive proteins selected from the group consisting of CTLA4 (herein e.g. Ipilimumab-Yervoy®), PDL1 (herein e.g. Nivolumab-Opdivo), PD1-L, also EpCam, IDO, MIC, Fas and TRAIL; specifically: as estrogen inhibitor for hormone positive patients from the group of aromatase inhibitors—(herein e.g. Letrozole and/or the estrogen blocker Fulvestrant); as antibody against HER2 positive patients: Herceptin (TDM-1) as a second preparation.

Also disclosed is a business method comprising marketing 4 to 7 HLA-A antigen peptides and at least 2 antigen peptides corresponding to MHC class II complexes for the treatment of breast cancer in a human to effectively reduce the CA 15-3 score of a patient or group of patients having at least one identical HLA allele, in particular to increase progression-free survival or reduce the likelihood of cancer recurrence or increase patient survival. In some embodiments, the marketing is followed by treatment of the patient with the combination of HLA antigen peptides.

BRIEF DESCRIPTION OF THE DRAWINGS

Herein shows.

EXEMPLARY EMBODIMENTS

Figure 1:
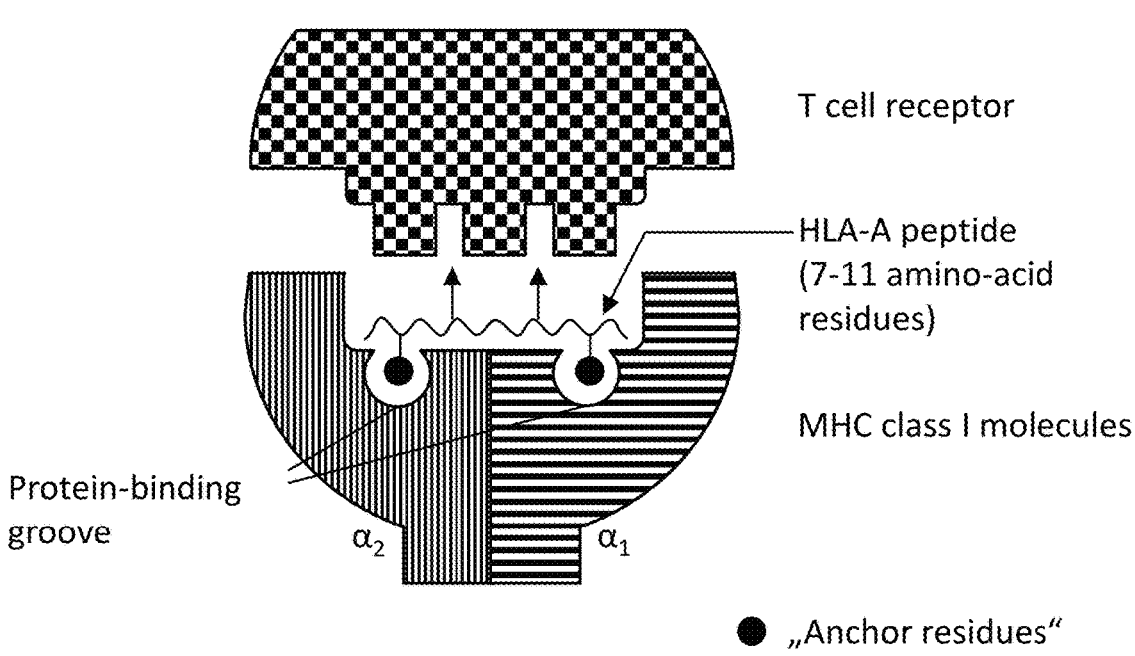
FIG. 1: Schematic representation of HLA-A-mediated binding of a T cell receptor to a class I MHC molecule, showing the anchor (amino acid) residues of the HLA-A antigenic peptide (7-11 amino acids in length).
Figure 2:
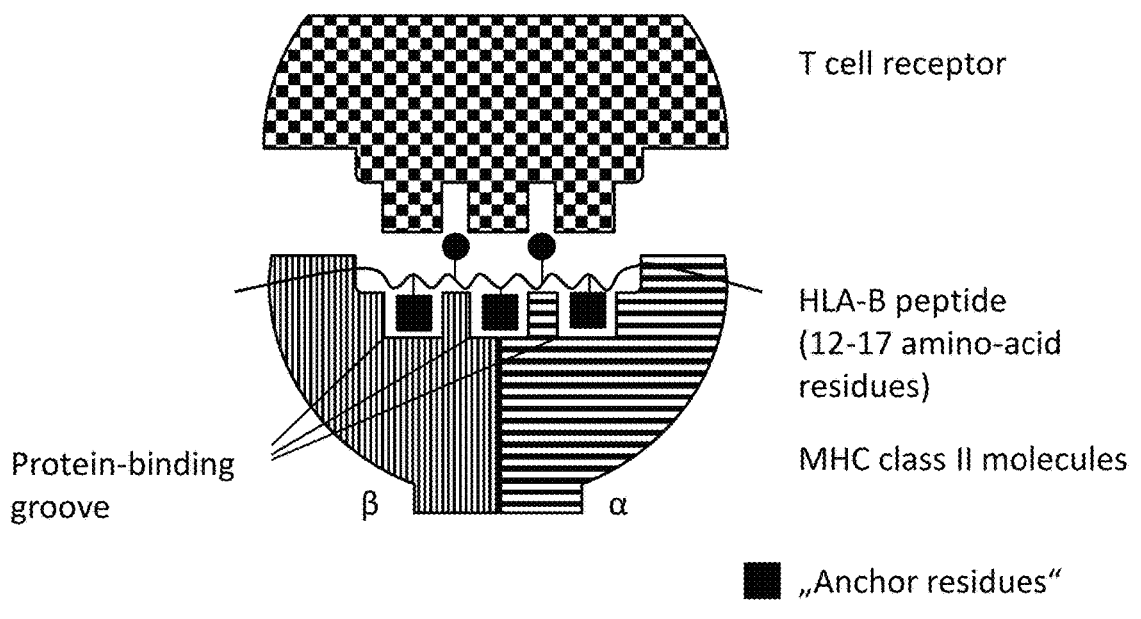
FIG. 2: Schematic representation of HLA-B-mediated binding of a T cell receptor to an MHC molecule, showing the anchor (amino acid) residues of the HLA-B antigenic peptide (12-17 amino acids in length).

With the aid of the following figures and embodiments, the present invention will be explained in more detail without limiting the invention to the same.

The following tables list HLA tumor antigen peptides, all of which have been tested and are immunogenic. SEQ ID Nos: 13 to 48 list some preferred, but not limiting, examples of amino acid sequences of tumor antigen peptides of the invention, each of which is another embodiment of the present invention.

TABLE 1

| [Comparison example]: | | | |
|---|---|---|---|
| Tumor antigenic peptide | Wild-type HLA peptide | specific activity towards T cell receptor [nM] | Target protein [Sequence position in the overall sequence of the protein] |
| HLA-A Antigenic peptide (Subtype: A29-02) (SEQ ID NO: 1) | CVGRRNYRFFY | 132.00 | ZDHHC18 p.C228Y |
| HLA-A Antigenic peptide (SEQ ID NO: 2) | HAVFVQSYY | 141.00 | SMAD 4 p.A406V |
| HLA-A Antigenic peptide (SEQ ID NO: 3) | LLDPEDVD | 20986.09 | PLEC p.D220Y |
| HLA-A Antigenic peptide (SEQ ID NO: 4) | HTDIYANY | 142.87 | PCSK1 p.T128M |
| HLA-A Antigenic peptide (SEQ ID NO: 5) | AVFVQSYY | 65.00 | SMAD4 p.A406V |
| HLA-B Antigenic peptide (SEQ ID NO: 6) | EEEAAAAAY | 147.31 | FBX02 p.E39A |
| HLA-B Antigenic peptide (SEQ ID NO: 7) | MEVLSQEIVR | 5407.15 | GRIPAP1 p.R822W |
| HLA-B Antigenic peptide (SEQ ID NO: 8) | HMKKMMKDL | 131.67 | STIM1 p.D247A |
| HLA-C Antigenic peptide (SEQ ID NO: 9) | SSTALHPCPF | 180.82 | PRR21 p.A63P |
| HLA-C Antigenic peptide (SEQ ID NO: 10) | LSYLHVHTA | 283.98 | STS p.L284F |

TABLE 1-continued

[Comparison example]:

| Tumor antigenic peptide | Wild-type HLA peptide | specific activity towards T cell receptor [nM] | Target protein [Sequence position in the overall sequence of the protein] |
|---|---|---|---|
| HLA-C Antigenic peptide (SEQ ID NO: 11) | YSLLSLLHT | 1550.46 | STK40 p.T107M |
| HLA-C Antigenic peptide (SEQ ID NO: 12) | CPFTHGSSPM | 160.14 | PRR21 p.C67Y |

TABLE 2

| Neoantigen peptide (Subtype) | Amino acid sequence of the neoantigen peptide | Wild-type HLA peptide (comparative example) | Amino acid ex-change | specific activity towards T cell receptor [nM] | Target protein [Sequence position in the total sequence of the protein] |
|---|---|---|---|---|---|
| HLA-A Neoantigen peptide (Subtype: A01.01; A29.02; C16.01) (SEQ ID NO: 13) | YVGRRNYRFFY | CVGRRNYRFFY | C/Y | 16.00 | ZDHHC18 [228-238] p.C228Y |
| HLA-A Neoantigen peptide (Subtype: A01.01; A29.02) (SEQ ID NO: 14) | HVVFVQSYY | HAVFVQSYY | A/V | 32.00 | SMAD 4 [405-413] p.A406V |
| HLA-A Neoantigen peptide (Subtype: A01.01) (SEQ ID NO: 15) | LLDPEDVY | LLDPEDVD | D/Y | 45.67 | PLE [372-379] p.D379Y |
| HLA-A Neoantigen peptide (Subtype: A01.01; A29.02) (SEQ ID NO: 16) | HMDIYANY | HTDIYANY | T/M | 24.97 | PCSK1 [174-181] p.T175M |
| HLA-A Neoantigen peptide (Subtype: A01.01; A29.02) (SEQ ID NO: 17) | VVFVQSYY | AVFVQSYY | A/V | 18.00 | SMAD4 [406-413] p.A406V |
| HLA-A Neoantigen peptide (TSA) (Subtype: A02.01, B18.01) (SEQ ID NO: 18) | DEDEIKWWW | DEDEIEWWW | E/K | 9.77 | TP53BP2 [1091-1099] p.E1096K |
| HLA-A Neoantigen peptide (TSA) (Subtype: A02.01) (SEQ ID NO: 19) | FVNDKFMPL | FVNDKFMPP | P/L | 12.73 | ZC3H12A [269-277] p.P277L |
| HLA-B Neoantigen peptide (Subtype: A01.01; B44.03) (SEQ ID NO: 20) | EEAAAAAAY | EEEAAAAAY | E/A | 41.45 | FBXO2 [37-46] p.E39A |
| HLA-B Neoantigen peptide (Subtype: A01.01; B44.03) (SEQ ID NO: 21) | MEVLSQEIVW | MEVLSQEIVR | R/W | 25.66 | GRIPAP1 [813-822] p.R822W |
| HLA-B Neoantigen peptide (Subtype: A01.01; B08.01) (SEQ ID NO: 22) | HMKKMMKAL | HMKKMMKDL | D/A | 16.48 | STIM1 [240-248] p.D247A |
| HLA-C Neoantigen peptide (Subtype: A01.01; C16.01) (SEQ ID NO: 23) | SSTPLHPYPF | SSTALHPCPF | A/P | 44.19 | PRR21 [60-69] p.A63P |
| HLA-C Neoantigen peptide (Subtype: A01.01; C16.01) (SEQ ID NO: 24) | FSYLHVHTA | LSYLHVHTA | L/F | 38.46 | STS [284-292] p.L284F |

TABLE 2-continued

| Neoantigen peptide (Subtype) | Amino acid sequence of the neoantigen peptide | Wild-type HLA peptide (comparative example) | Amino acid ex-change | specific activity towards T cell receptor [nM] | Target protein [Sequence position in the total sequence of the protein] |
|---|---|---|---|---|---|
| HLA-C Neoantigen peptide (Subtype: A01.01; C16.01) (SEQ ID NO: 25) | YSLLSLL<u>HM</u> | YSLLSLLHT | T/M | 42.42 | STK40 [99-107] p.T107M |
| HLA-C Neoantigen peptide (Subtype: C16-01) (SEQ ID NO: 26) (B08.01) | <u>YP</u>FTHGSSPM | CPFTHGSSPM | C/Y | 30.96 | PRR21 [67-76] p.C67Y |

TABLE 3

| | Amino acid sequence of the HLA tumor antigen peptide | Amino acid exchange | specific activity towards T cell receptor [nM] | Target protein [Sequence position in the total sequence of the protein] |
|---|---|---|---|---|
| Klasse I HLA-A Antigen peptide (Subtype: A24) (SEQ ID NO: 27) | TYLPTNASLSF | — | 137.50 | ERB2 [63-72] |
| Klasse I HLA-Antigen peptide (Subtype: B51.01) (SEQ ID NO: 28) | DAVIVKLEI | — | 7376.79 | PKD2 [861-869] |
| Klasse I HLA-Antigen peptide (Subtype: A24.02) (SEQ ID NO: 29) | YYLDLS<u>I</u>TR | R/I (p.R397I) | 3674.81 | PKD2 [391-399] |
| Klasse I HLA-A Antigen peptide (Subtype: A02) (SEQ ID NO: 30) | ILFGISLREV | — | 13.61 | MAGEC1 [26-35] |
| Klasse I HLA-A Antigen peptide (Subtype: A02.01) (SEQ ID NO: 31) | KVVEFLAML | — | 58.22 | MAGEC1 [150-158] |
| Klasse I HLA-A Neoantigen peptide (Subtype: A02.01) (SEQ ID Nr.: 32) | FVNDKFMP<u>L</u> | P/L p.P277L | 12.73 | ZC3H12A [269-277] |
| Klasse I HLA-A Neoantigen peptide (Subtype: A02.01) (SEQ ID Nr.: 33) | FLLILKRD<u>S</u> | N/D p.N104D | 10793.42 | ENTHD2 [96-105] |
| Klasse I HLA-A Neoantigen peptide (Subtype: A02.01) (SEQ ID Nr.: 34) | RTPLSA<u>L</u>CV | P/L p.P92L | 7172.33 | ASIP [86-94] |
| Klasse I HLA-B Neoantigen peptide (Subtype: B18.01) (SEQ ID Nr.: 35) | DEDE<u>I</u>KWWW | E/K p.E1096K | 9.77 | TP53BP2 [1091-1099] |

TABLE 4

| | Amino acid sequence of the HLA tumor antigen peptide | Amino acid exchange | Target protein [Sequence position in the total sequence of the protein] | another target haplotype | Immunogenic (+ . . . highly immunogenic |
|---|---|---|---|---|---|
| Class II HLA-Neoantigen peptide (SEQ ID Nr: 36) | EDKKIDFSEFLSLLGDI | — | S100A7 [66-82] | | + |
| Class II HLA-Neoantigen peptide (SEQ ID Nr: 37) | IHREDEDEIKWWWARLN | E/K p.E1096K | TP53BP2 [1087-2003] | | + |
| Class II HLA-Neoantigen peptide (SEQ ID Nr: 38) | STKYSHKSPQLSVHVTD | Y/H p.Y129H | CD33 [124-140] | | + |
| Class II HLA-Antigen peptide (SEQ ID Nr: 39) | KYIQESQALAKRSCGLFQ KLGEYYLQNAFL | — | AFP [403-432] | | + |
| Class II HLA-Antigen peptide (SEQ ID Nr: 40) | VDLIVEYEAFPKPE | — | KIT [331-344] | | + |
| Class II HLA-Neoantigen peptide DRB1.09*01 (SEQ ID Nr: 41) | ATYSGAGYYLDLSIT | R/I p.R3971 | PKD2 [384-398] | | + |
| Class II HLA-Neoantigen peptide DRB1.16*01 (SEQ ID Nr: 42) | HGSSFFLLILKRDSAFI | N/D p.N104D | ENTHD2 [92-108] | | + |
| Class II HLA-Neoantigen peptide (Subtype: DRB1*03) (SEQ ID Nr: 43) | YSMKCKNVVPLNDLLLE | p.Y537N | ESR1 [526-542] | auf Subtype A01 | + |
| Class 11 HLA-Neoantigen peptide (Subtype: DRB1*03) (SEQ ID Nr: 44) | PLQIILMPQVQPGLP | p.P931L | SMG8 [918-932] | auf Subtype A01 | + |
| Class II HLA-Neoantigen peptide (Subtype: DRB1*03) (SEQ ID Nr: 45) | LLHTEYSLLSLLHMQ | p.T102M | STK40 [89-103] | auf Subtype A01 | + |
| Class II HLA-Neoantigen peptide (Subtype: DRB1*03) (SEQ ID Nr: 46) | NYLAEEITVDVRDEF | p.E625A | STON2 [622-636] | auf Subtype A01 | + |
| Class II HLA-Neoantigen peptide (Subtype: DRB1*07) (SEQ ID Nr: 47) | REIDVLERELNVLIF | | KIAA1804 | auf Subtype A01 | + |
| Class II HLA-Antigen peptide (Subtype: DRB1*07) (SEQ ID Nr: 48) | PSNYQPHQACRITFL | p.PPSMQNHIP 1575-1583 HQACRITFL | ARID1A [1569-1583] | auf Subtype A01 | + |

Example 1: Transcriptome Analysis [mRNA Expression]

Transcriptome analysis (sequencing) was performed in all patients using PANTHER chip analysis (44K chip) from Agilent Technologies. The 44K chip used contains 44,000 gene probes, so that the activity of >34,000 gene expression markers could be analyzed with this chip per patient in each case. In each case, 1,000 genes with increased relevance were determined 10-fold.

The evaluation is based on published gene signatures known to the expert.

Example 2: EXOM Sequencing

Exome sequencing is performed from the standard frozen specimen of the patients from whom the tumor DNA is extracted. Next-generation sequencing of the exome is performed from the tumor sample with coverage of more than 95% of the entire human coding exon region. For this purpose, among others, >290,000 relevant sections of DNA are selectively amplified and sequenced by semiconductor sequencing technology.

The aim of the analysis is to define possible mutations for the design of an individual tumor antigen peptide immunization. To exclude non-tumor associated variants (SNPs, Single Nucleotide Polymorphism) of the germline, DNA is simultaneously isolated from nucleated blood cells of the patients and comparatively sequenced using the same methodology. The differentiation of potential neoantigen candidates was performed in the following six steps:

1) Selection of tumor/somatic mutations is reduced by exclusion of non-tumor specific polymorphisms.
2) The predefined selection of somatic mutations is further restricted to quality parameters, read coverage and influence on the protein sequence. More complex mutations than single amino acid substitutions SNPs, and mutations in non-protein coding regions are excluded. Silent mutations are also excluded.
3) The mutations defined in this way are expanded to flanking 20s oligopeptides using the known protein sequences (RefGene database). From these, 12×9 oligopeptides each were formed sequentially and the affinity to the pre-known, patient-specific hypervariable HLA-I paratopes was determined (program NetMHC-4.0). Nonapeptides with high affinity to the paratopes, which show a further increase in affinity compared to the wild type sequence due to the mutation (SNP), were selected.

4) Candidates carrying this mutation as a germline mutation in an exome pool at the same position are excluded (NIH-NHLBI 6500 exome database version-2 program ANNOVAR-Tool2.)

5) Based on the results of the expression analysis (see findings under embodiment example 1), peptides with a low expression relevance in the tumor can be excluded.

6) Finally, we will examine in detail whether further polymorphisms may be present in the vicinity of the single base exchange and thus represent further, patient-specific deviations from the hg19 defined genome sequence.

The following is an example of the evaluation of the results of the described mutation analysis and filtration steps for one patient:

1) Comparison of tumor DNA versus normal DNA
a. "Exome_single_sample_Somatic" using the IonReporter yields:
37494 variants in normal DNA, and
37299 variants in tumor DNA.
The paired analysis "AmpliSeq Exome tumor-normal pair" detects and annotates rare somatic variants (SNPs, InDels, CNVs) using statistical analysis in the Ion AmpliSeq Exome Panel (Ion Reporter Software 4.6. Workflow Version: 1.0). This results in: 1477 mutations in the tumor with concurrent wild type categorization in the normal DNA.
These 1477 variants are the starting point for further restrictions.

2) Restriction of variants to protein-coding SNP (single nucleotide polymorphisms) with amino acid substitution.
Restriction to SNPs
At least 50× sequenced in tumor and min. 20× sequenced in blood
Must not have occurred in the blood in any single run
Must be positioned in an exon
Must result in amino acid exchange (missense mutation)

3) From these variants, 20s peptides are defined and fed to the HLA paratope affinity analysis NetMHC.
~25*12 nonapeptide pairs (each mutant and wild type) are submitted to affinity analysis for analysis in 9 HLA loci each. Out of these 5814 affinities (2907 pairs) are analyzed. In 40 pairs, an affinity at least 2-fold higher in the mutated peptide than in the wild-type peptide is detected.
Summary of Variants with Increased HLA Affinity 4) Candidates that carry this mutation as a germline mutation at the same position in an exome pool (NIH-NHLBI 6500 exome database version-2) are excluded (Programm ANNOVAR-Tool3.)
Database filters used: hg19_esp6500siv2_all 5) Selection from remaining 25 variants with significant mRNA expression (>3 fold versus normal tissue) in alignment with transcriptome Example 3: Patients with mMC (Metastatic Breast Carcinoma), Type_HER2-Neu 1) Clinical History of the Patients
Patient, Female
Initial clinical findings: invasive ductal bifocal breast carcinoma (breast CA), right, tumor 2 cm to 5 cm in greatest extent (pT2), pN1sn pN1 (3/5) G2, NO, ER-, PR-, HER-2 new: 3+, Ki-67: 55%.
Treatment Procedure:
2 weeks later: Neoadjuvant chemotherapy (TCH w3) 6 cycles, trastuzumab;
6 months later: Irradiation of the right breast+lymphatic drainage area (LAG).
Tumor completely destroyed by radiotherapy or chemotherapy (CR=complete remission) of tumor, findings: patient discharged from hospital as cured.
Recurrence: Local recurrence with additional liver metastases (4 foci) occurs 24 months after initial diagnosis; findings: ER-, PR+(60%), HER-2 new: 3+, Ki-67: 80%.
This recurrent mammary/breast CA occurred with liver metastases and also had significantly greater aggressiveness (Ki-67: 80% versus 55% (initial finding)).
Prognosis of the clinicians: The patient was discharged from the hospital with a prognosis of OS (overall survival) expected/average of 6 months.
The well-known fact that in breast CA, second primary malignancy (SPM) flared up again is associated with worse prognosis and with worse OS (see "Breast cancer survivors face excess risk for second primary cancer in SEER analysis," Wei J L & al, Int J Clin Oncol, Mar. 19, 2019), likely triggered by prior chemotherapy,
Treatment Procedure:
2 months after diagnosis: surgical removal of the mammary gland and adjacent tissues of the right breast (mastectomy) because of a local recurrence that had occurred there.
4 months after diagnosis: Appearance of bone metastases (osseous metastases (spine)) and bronchial carcinoma (suspicious LK pulmonary hilus);
9 months after diagnosis: surgical removal of the mammary gland and adjacent tissues of the left breast.
Tumor progression despite trastuzumab or T-DM1 continuous therapy 2) Individualized Immune Information Therapy: Analytics
After therapy/treatment procedures under point 1 had been carried out without success, the immunological therapy approach of informing the patient's own immune system by means of application of tumor-associated and tumor-specific HLA antigen peptides in the form of synthesized peptides was used as part of a curative trial.
The focus was on the cellular immune defense, i.e. the activation of the endogenous cytotoxic CD8+ T cells, which as naive T cells are able to recognize virtually all conceivable pathogenic as well as malignant amino acid sequences (the so-called "targets") by means of a highly differentiated receptor system and thus develop into effector cells. These effector T cells can destroy the tumor cells recognized via the HLA-present antigens by secreting granzyme and perforin.
For this purpose, data were collected from biopsied tumor tissue of the patients via "next generation sequencing" (NGS) and "liquid chromatography-coupled tandem mass spectrometry" (LC-MS/MS) using the following three steps
the mRNA expression of all coding gene regions (transcriptome—step (a)), the tumor-specific somatic miss-sense mutations as well as via (exome sequencing—step (b))

the HLA-restricted ligands of the HLA classes I+II presented by the tumor cells (HLA ligandome—step (c))

to step (a): The mRNA expression data (approximately 40,000) were compared with the expression levels of healthy tissue and filtered with respect to significant (>3-fold) deviation of the expression values, and further with regard to the significance of the genes concerned for tumor development according to the criterion that these genes may not be expressed or only slightly expressed in other tissue types furthermore, with regard to the group of cancer-testis antigens, which are generally not expressed in healthy mammary tissues of adults, notable expressions in the tumor were recorded, since these may have the quality of a tumor-specific antigen This resulted in a separate data set of possible HLA tumor antigen peptides (number 86), which were weighted with respect to their expression abnormalities/deviations from normal and their known importance for tumor proliferation-→factor 3 vs. normal; importance for tumor development: growth factors, angiogenesis factors, metastasis factors.

to step (b): The somatic miss-sense mutations (single nucleotide variants (SNV) with an exchange of one amino acid as well as frame-shift mutations) (number: 57) were combined in another data set, since they are potentially significant (neo)-antigens in character and thus highly tumor-specific.

to step (c): The HLA-restricted ligands (amino acid sequences of 9-10 AS (corresponding to MHC class I complexes) (number:1100) and sequences of 12-15 AS (corresponding to MHC class II complexes) (number: 730) were screened using information from specialized databases for already appeared in healthy tissue (=negative)

In protein match with promising sequences from transcriptome and exome, whether sequences of the identified tumor-associated HLA antigen peptides are associated with proliferation, invasiveness, angiogenesis, and/or an increase in cytokeratin production of mammary/breast carcinoma.

In parallel to these described tumor tissue examinations, the genetic haplotype, the alleles of the HLA antigen peptides corresponding to the patient's MHC class I complexes were determined. The patient-individual result resulted in the following assignment:

HLA-A*02:01, A*24:02, B*18:01, B*51:01, C*07:01, C*15:02; HLA-DRB1*09:01; DRB1*16:01, DQB1*03:03, DQB1*05:02.

(With the support of HLA-A*02:01 in connection wirh B*18:01 this patient represents about 40% of the population living in Europe (Caucasian)).

3) Individualized Immune Information Therapy: Target Selection to step (a): From the data sets of the transcriptome, amino acid sequences of the respective proteins were first used to select amino acid sequences of the HLA tumor antigen peptides corresponding to the MHC complexes (nonamers) with the highest allelic affinities (specific activity towards T cell receptor [nM]). This selection criterion is used to algorithmically determine the probability with which the respective HLA tumor antigen peptide is presented in vivo on the corresponding MHC complexes (a first prerequisite for a possible cellular immune response).

to step (b): From the data sets of the mutation tests, nonameric variants involving amino acid exchange were determined with respect to the highest affinities (specific activity towards T cell receptor [nM]) based on the alleles of the patient. Also, polymers of 17 amino acids (oligopeptides) were determined under the affinity criterion for this purpose. This selection criterion algorithmically determines the probability with which the respective tumor antigen peptide corresponding to the MHC complexes is presented in vivo on the corresponding MHC complexes (a second prerequisite for a possible cellular immune response).

step (c): Based on the new data sets identified in step (a) and (b), with the addition of the HLA-restricted ligands (the data set of the ligandome), a selection of HLA tumor antigen peptides corresponding to MHC class I complexes and corresponding to MHC class II complexes was made, which were the most promising epitope candidates for eliciting a cellular immune response, both individually and especially in their combination.

4) Individualized Immune Information Therapy: Peptide Synthesis and Delivery Solution step (a): The peptide concepts selected for the custom application solution were synthesized as chemical peptides.

step (b): the following 7 HLA-A tumor antigen peptides corresponding to MHC class I complexes and 2 HLA tumor antigen peptides corresponding to MHC class II complexes were mixed in a 33% DMSO/H$_2$O application solution and divided into 24 vial units of 1 ml each.

Sequences of the Nine Tumor Antigen Peptides

| Nr. | Amino acid sequence | Identification number | Class |
|---|---|---|---|
| 1 | ILFGISLREV | SEQ-ID Nr.: 30 | HLA-A |
| 2 | KVVEFLAML | SEQ-ID Nr.: 31 | HLA-A |
| 3 | DEDEIKWWW | SEQ-ID Nr.: 35 | HLA-B |
| 4 | FVNDKFMPL | SEQ-ID Nr.: 32 | HLA-A |
| 5 | TYLPTNASLSF | SEQ-ID Nr.: 25 | HLA-A |
| 6 | FLLILKRDS | SEQ-ID Nr.: 33 | HLA-A |

-continued

| Nr. | Amino acid sequence | Identification number | Class |
|---|---|---|---|
| 7 | DAVIVKLEI | SEQ-ID Nr.: 28 | HLA-A |
| 8 | RTPLSALCV | SEQ-ID Nr.: 34 | HLA-A |
| 9 | EDKKIDFSEFLSLLGDI | SEQ-ID Nr.: 36 | class II |
| 10 | STKYSHKSPQLSVHVTD | SEQ-ID Nr.: 38 | class II |
| 11 | HGSSFFLLILKRDSAFI | SEQ-ID Nr.: 42 | class II |
| 12 | KYIQESQALAKRSCGLFQKLGEYYLQNAFL | SEQ-ID Nr.: 39 | Klasse II (Oligopeptide) |

Dose per tumor antigen peptide: 500 μg

5) Individualized Immune Information Therapy: Application Protocol

Pretreatment: 300 mg/m² cyclophosphamide (single infusion); 3 days before first injection Application: intra-dermal (i.d.)

Application site: left and right upper arm

Administration plan: 23 vaccinations on days 1, 2, 3, 8, 15, 22, 36, 50, 71 and on every 3 weeks until day 365.

Adjuvants added per application: 12.5 mg imiquimod in 250 mg cream (Aldara) topically at injection site; 200 μg ipilimumab (Yervoy), because CTLA4 elevated, alternating with 300 μg nivolumab (Opdivo), because PD1 or PD-L1 elevated, subcutaneously (s.c.) directly adjacent to application site 6) Individualized Immune Information Therapy: 2 Evidences of Clinical Effects.

Figure 3:
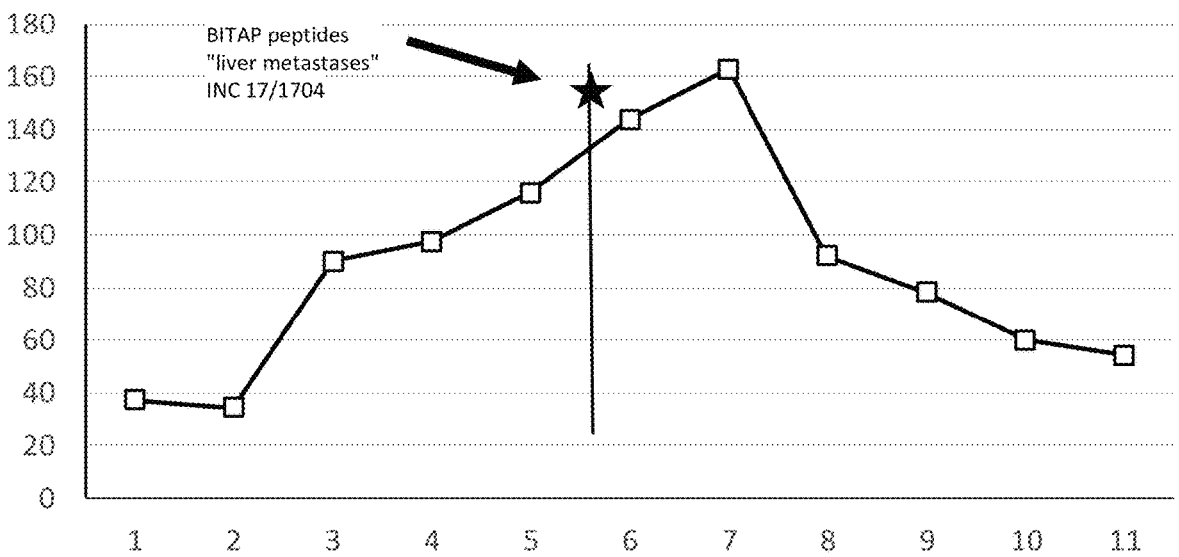
FIG. 3: the development of the specific tumor marker CA 15-3 after specific immune information by the composition according to the invention of tumor antigen peptides according to embodiment 3 (INC 14/1713; star), which depict the epitopes of the primary tumor MC-HER2/Neu. The course depicted comprises 26 weeks.
Figure 4:
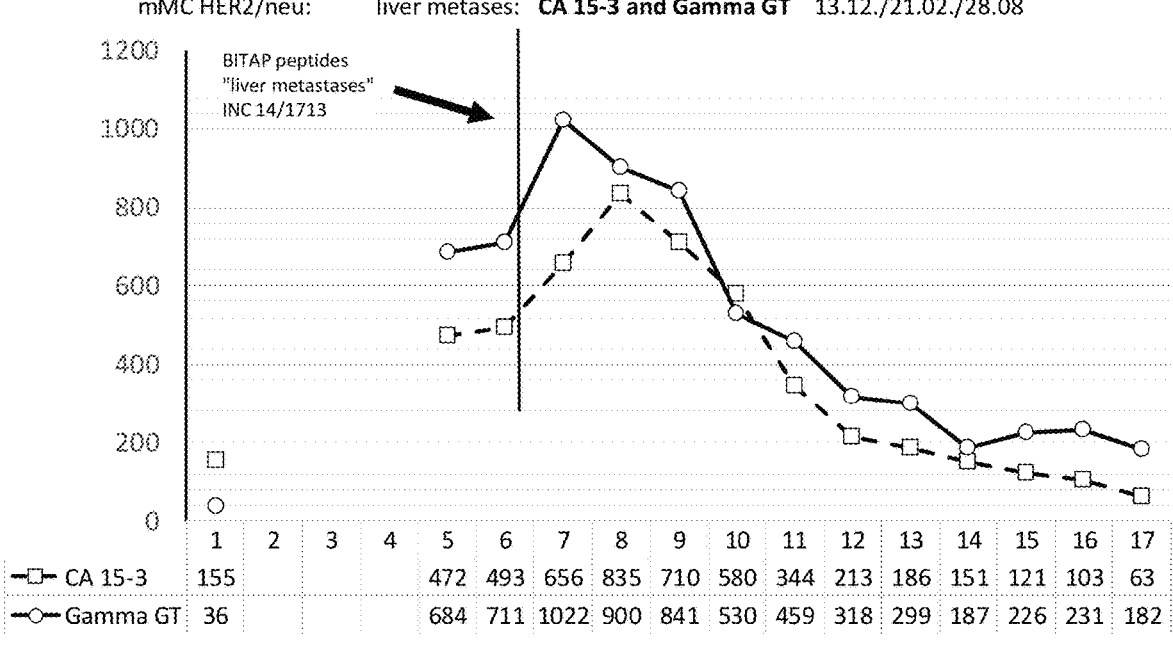
FIG. 4: the development of the specific tumor marker CA 15-3 in combination with the liver marker Gamma GT after application of specific immune information by the composition of tumor antigen peptides according to embodiment 3 (INC 14/1713; vertical line), which represent the specific metastatic epitopes of the liver metastases of the scattered MC-HER2/Neu. The imaged course covers 34 weeks.

Based on two significant examples, the clinical efficacy of the applied immunotherapy in the presented case 1 can be shown below:

FIG. 3 shows the evolution of the Specific Tumor Marker CA 15-3 in combination with the liver marker Gamma GT after specific application (i.d.) specific pharmaceutical composition of immune information by BITAP peptides (star line), which are the specific metastatic epitopes of liver metastases of the scattered mMC-HER2/New (INC 14/1713).

The course shown covers 34 weeks.

the development of the specific tumor marker CA 15-3 after specific immune information by the composition according to the invention of tumor antigen peptides (star) mapping the epitopes of the primary tumor MC-HER2/Neu (INC 14/1713). The course shown covers 26 weeks.

Beispiel 4: Patients with mIBC with lymphangosis carinomatosis (metastatic inflammatory breast cancer)

1) Clinical History of the Patients

Patient, Female (46 Years)

The initial clinical findings: inflammatory breast carcinoma right with extensive lymphangiosis carcinomatose; Initial tumor stage pT4, pn3a (24/29)(Level 11:14/19, Level III: 10/10), MO, L1, VO, G2. HR+, PR+, Androgenr.+, HER2/neu–

Recurrence: Postoperatively, a first recurrence already after 3 months: Progression of findings intramammary in the area of the right lower quadrant with significant increase in consistency of the breast tissue. Skin infiltration crossing the midline in the area of the thoracic wall as well as locoregional tumor infiltration of the axillary adipose tissue and the lateral thoracic wall along the pectoralis major muscle on the right.

After 5 months locoregional tumor recurrence, with extension into the axilla.

Chemotherapy from month 6 to month 11, discontinued after 5 cycles if tumor progression during chemotherapy. Locoregional tumor recurrence, 7×11 cm along ventrolateral thoracic wall. Skin and subcutaneous tissue extensively infiltrated and thickened.

Hormone therapy with aromatase inhibitor and irradiation of the right breast, chest wall and supraclavicular/cervical right side.

Prognosis of the clinicians: Overall survival for an expected 3-4 months. (Inflammatory breast carcinoma is a relatively rare, particularly aggressive form of breast carcinoma, which in this case 2 had already spread to the lymphatics (24 of 29 lymph nodes were already affected at initial diagnosis)).

Treatment process according to the invention: After all therapies available in the standard and regular canon of oncological medicine had been carried out without success, the immunological therapy approach of informing the patient's own immune system by means of application of tumor-associated and tumor-specific antigens in the form of synthesized peptides was used in the context of a curative trial.

The focus was on the cellular immune defense, i.e. the activation of the endogenous cytotoxic CD8+ T cells, which as naive T cells are able to recognize virtually all conceivable pathogenic as well as malignant amino acid sequences (hereinafter the "targets") by means of a highly differentiated receptor system and thus develop into effector cells. These effector T cells can destroy the tumor cells recognized via the HLA-present antigens by secretion of granzyme and perforin.

Activation of these immune cells occurs via HLA class I ligands, i.e. antigens presented as sequences of 8-10 amino acids restricted on class I HLA molecules.

In months 14-84 after initiation of individualized immunoinformatics therapy, additional local recurrences (lymph nodes) occurred, each of which was surgically removed. However, distant metastasis was prevented.

2) Individualized Immune Information Therapy: Analytics

To identify tumor-associated and tumor-specific antigen peptides, data were determined from biopsied tumor tissues of the patients using next generation sequencing (NGS) and liquid chromatography-coupled tandem mass spectrometry (LC-MS/MS) in the following three steps:

the mRNA expression of all coding gene regions (transcriptome—step (a)), the tumor-specific somatic miss-sense mutations as well as via (exome sequencing—step (b))

the HLA-restricted ligands of the HLA classes I+II presented by the tumor cells (HLA ligandome—step (c))

to step (a): The mRNA expression data (approximately 40,000) were compared with the expression levels of healthy tissue and filtered with respect to significant (>3-fold) deviation of the expression values, and further the significance of the genes concerned for tumor development the criterion that these genes may not be expressed or only slightly expressed in other tissue types furthermore, with regard to the group of cancer-testis antigens, which are generally not expressed in healthy mammary tissues of adults, notable expressions in the tumor were recorded, since these may have the quality of a tumor-specific antigen This resulted in a separate data set of possible HLA tumor antigen peptides (number 86), which were weighted with respect to their expression abnormalities/deviations from normal and their known importance in tumor proliferation.

to step (b): The somatic miss-sense mutations (single nucleotid variants (SNV) with an exchange of one amino acid as well as frame-shift mutations) (number: 41) were combined in another data set, since they are potentially significant (neo)-antigens in character and thus highly tumor-specific.

to step (c): The HLA-restricted ligands (amino acid sequences of 9-10 AS (corresponding to MHC class I complexes) (number:1321) and sequences of 12-15 AS (corresponding to MHC class II complexes) (number: 863) were screened using information from specialized databases for already appeared in healthy tissue (=negative)

protein match with promising sequences from transcriptome and exome, whether sequences of the identified tumor-associated HLA antigen peptides are associated with proliferation, invasiveness, angiogenesis, and/or an increase in cytokeratin production of mammary/breast carcinoma.

In parallel to these described tumor tissue examinations, the genetic haplotype, the alleles of the HLA antigen peptides corresponding to the patient's MHC class I complexes were determined. The patient-individual result resulted in the following assignment:

HLA-A*01:01, A*29:02, B*08:01, B*44:03, C*07:01, C*16:01; HLA-DRB1*03:01; DRB1*07:01, DRB3*01:01, DRB1*03:01, DRB4*01:01, DQB1*02: 01, DPB1*01:01

(With the support of HLA-A*01:01 in connection with B*08:01 this patient represents about 25% of the population living in Europe (Caucasian)).

3) Individualized Immune Information Therapy: Target Selection to step (a): From the data sets of the transcriptome, amino acid sequences of the respective proteins were first used to select amino acid sequences of the HLA tumor antigen peptides corresponding to the MHC complexes (nonamers) with the highest allelic affinities (specific activity towards T cell receptor [nM]). This selection criterion is used to algorithmically determine the probability with which the respective HLA tumor antigen peptide is presented in vivo on the corresponding MHC complexes (a first prerequisite for a possible cellular immune response).

to step (b): From the data sets of the mutation tests, nonameric variants involving amino acid exchange were determined with respect to the highest affinities (specific activity towards T cell receptor [nM]) based on the alleles of the patient. Also, polymers of 17 amino acids were determined under the affinity criterion for this purpose. This selection criterion algorithmically determines the probability with which the respective tumor antigen peptide corresponding to the MHC complexes is presented in vivo on the corresponding MHC complexes (a second prerequisite for a possible cellular immune response).

step (c): used on the new datasets identified in step (a) and (b), with the addition of the HLA-restricted ligands (the dataset of the ligandome), a selection was made of HLA tumor antigen peptides corresponding to MHC class I complexes and corresponding to MHC class II complexes that were the most promising epitope candidates for eliciting a cellular immune response, both individually and, most importantly, in combination.

4) Individualized Immune Information Therapy: Peptide Synthesis and Delivery Solution step (a): The peptide concepts selected for the custom application solution were synthesized as chemical peptides.

step (b): the following 9 HLA-A tumor antigen peptides corresponding to MHC class I complexes and 2 HLA tumor antigen peptides corresponding to MHC class II complexes were mixed in a 33% DMSO/H$_2$O application solution and divided into 6 vial units of 1.5 ml each.

Sequences of the Nine Tumor Antigen Peptides

| Nr. | Amino acid sequence | Identification number | Class |
|---|---|---|---|
| 1 | LLDPEDVY | SEQ-ID Nr.: 15 | HLA-A |
| 2 | HVVFVQSYY | SEQ-ID Nr.: 14 | HLA-A |
| 3 | HMDIYANY | SEQ-ID Nr.: 16 | HLA-A |
| 4 | YVGRRNYRFFY | SEQ-ID Nr.: 13 | HLA-A |
| 5 | VVFVQSYY | SEQ-ID Nr.: 17 | HLA-A |
| 6 | HMKKMMKAL | SEQ-ID Nr.: 22 | HLA-B |
| 7 | EEAAAAAAAY | SEQ-ID Nr.: 20 | HLA-B |
| 8 | SSTPLHPYPF | SEQ-ID Nr.: 23 | HLA-B |
| 9 | MEVLSQEIVW | SEQ-ID Nr.: 21 | HLA-B |
| 10 | YSMKCKNVVPLNDLLLE | SEQ-ID Nr.: 43 | class II |
| 11 | NYLAEETVDVRDEF | SEQ-ID Nr.: 46 | class II |
| 12 | LLHTEYSLLSLLHMQ | SEQ-ID Nr.: 45 | class II |

Dose per peptide: 300 μg

Total peptide content per application dose (vial): 3.3 mg

5) Individualized Immune Information Therapy: Application Protocol

Pretreatment: 3 million units of IFN alpha 2b (Roferon), 4 days before first injection Application: subcutaneous (s.c.)

Application site: left and right upper arm, left and right hip

Administration plan: 6 injections on days 1, 8, 22, 50, 180 and 360

Adjuvants added per application: Montanide ISA 51 VG (1.5 ml), mix 1:1 with peptide-vial (1.5 ml); 300 μg nivolumab (Opdivo), as PD1 or PD-L1 elevated, subcutaneous (s.c.) directly adjacent to injection site, 30 min before peptide/montanide injection.

6) Individualized Immune Information Therapy: Evidence of Clinical Effects

Figure 5:
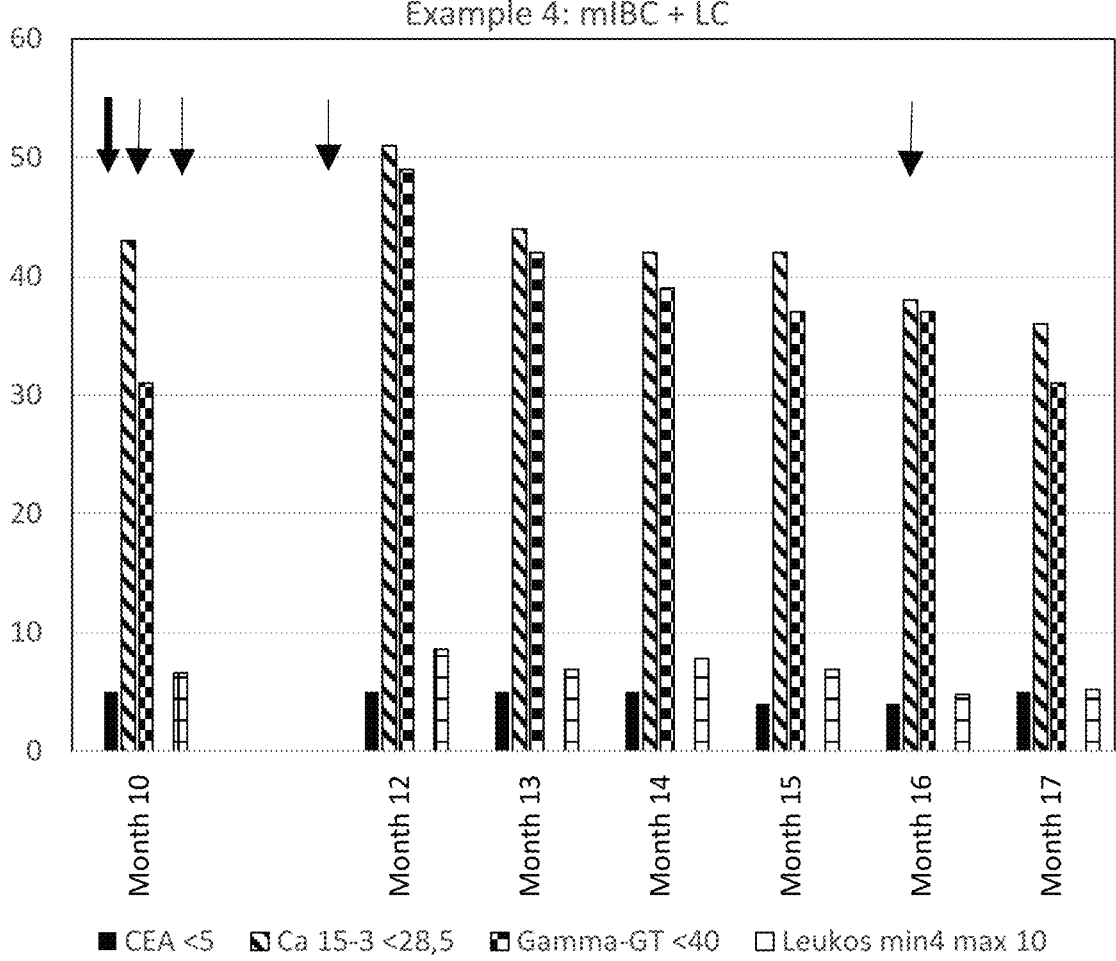
FIG. 5: The clinical efficacy of the applied pharmaceutical composition of embodiment 4.

The clinical efficacy of the applied immunotherapy in the illustrated embodiment 4 is shown in FIG. 5.

The graph represents the development of the tumor markers CEA (bar 1) and CA15-3 (bar 2) as well as the liver value gamma-GT (bar 3) and the leukocyte count (bar 4) during a period of 8 months after application of the pharmaceutical composition according to embodiment 4. This was preceded by aggressive tumor progression—essentially based on inflammatory lymphangiosis carcinomatosis. The application was performed with a 1:1 mixture of Montanide ISA 51 VG with the peptide cocktail. The volume was 3 ml and was applied s.c. at the 4 different application loci (see pt 5). In this peptide composition, it is the initial application (followed by 4 further applications; see arrows in FIG. 5).

The 10 peptides contained in the pharmaceutical composition according to embodiment 4 are tumor antigen peptides (or neoantigens). By information, antigens Nos. 1-4 and 10 have become epitopes, i.e. succeeded in activating the corresponding T cell receptors (TCR) and developing effector and memory cells

---

The invention claimed is:

1. A method for determining pharmaceutically active human leukocyte antigen (HLA) tumor antigen peptides for use in treatment or prophylaxis of mammary/breast carcinomas or in a composition for use in the treatment or prophylaxis of mammary/breast carcinomas, in particular locally recurrent or metastatic breast carcinomas in a patient or group of patients suffering from or suspected of suffering from mammary/breast carcinoma, comprising a pharmacologically effective amount comprising 4 to 8 HLA tumor antigen peptides corresponding to major histocompatibility complex (MHC) class I complexes and at least 2 tumor antigen peptides corresponding to MHC class II complexes, characterized in that the HLA tumor antigen peptides are tumor-exclusive or tumor-associated HLA antigen peptides, in particular those associated with mammary/breast carcinomas, wherein the HLA tumor antigen peptides comprise sequences contained in the sequences SEQ ID NO: 13-SEQ ID NO: 26, SEQ ID NO: 28, SEQ ID NO: 29 and SEQ ID NO: 32-SEQ ID NO: 48, comprising monitoring a tissue resection of a patient or group of patients suffering from or suspected of suffering from mammary/breast cancer, the method comprising the following steps:

(a) providing a tissue sample of the patient or group of patients, wherein cells of the tissue sample express class I and/or class II MHC complexes and present them on their surface, wherein said method step (a) of providing the tissue sample does not itself comprise any surgical intervention in the patient or one of the patients of the group of patients;

(b) determining the following parameters using the provided tissue sample from step (a):

i) the transcriptome of the tissue sample provided, and comparison with the transcriptome of a healthy tissue sample from the patient or group of patients to determine up- and/or down-regulated mRNA sequences that differ by a factor of 3 from a threshold in the healthy tissue sample; and ii) the specific HLA haplotype of the patient or patient group; and iii) the exome sequence of the tissue sample provided, and comparing the exome of the provided tissue sample with the exome of a healthy tissue sample or with a gene database of the patient or patient group to determine somatic mutations, and determining the HLA tumor antigen peptides that have somatic mutations and are up- or down-regulated relative to the healthy tissue sample, determined in step (i); and determining the HLA tumor antigen peptides associated with proliferation, invasiveness, angiogenesis, and an increase in cytokeratin production of a mammary/breast carcinoma; and iv) the ligandome to determine the tumor antigen peptides presented on the surface of the cells of the mammary/breast carcinoma determined in step (iii); and v) the specific binding affinity of the HLA tumor antigen peptides determined in step (iv) against the corresponding MHC complex of the cell of the breast cancer by means of a database and/or a ranking algorithm, and vi) the immunogenicity of the HLA tumor antigen peptides determined in step (iv) by means of an immunogenicity test, in particular by Western blot, enzyme-linked immunosorbent assay (ELISA) techniques, in particular by enzyme-linked immunospot assay (ELISPOT), atomic force microscopy (AFM) or immunodetection with microscopic analysis;

(c) selecting HLA tumor antigen peptides that meet the criteria according to the parameters defined in step (b) and that are expressed in the cells of the provided tissue sample and presented on the surface of these cells;

administering, based on the selection of HLA tumor antigen peptides, a pharmaceutical composition comprising each individual HLA antigen peptide in the composition at an absolute concentration to a patient or a specifically identified group of patients having at least one identical HLA allele for the treatment or prophylaxis of mammary/breast carcinomas.

2. The method of claim 1, wherein, after providing the tissue sample from the patient or group of patients in step (a), the BRCA1 and BRCA2 genes are analyzed for the presence of mutations.

3. The method of claim 1, wherein the tissue sample provided in step (a) is the tissue sample of a mammary/breast carcinoma.

4. The method of claim 1, wherein determining whether the HLA antigen peptides are presented on the surface of the cells of the tissue sample of the patient or group of patients provided in step (a) is performed by ultra-high performance liquid chromatography (UHPCL) in conjunction with electrospray ionization (ESI) mass spectrometry (MS).

* * * * *